US007029868B2

(12) United States Patent
Sullivan et al.

(10) Patent No.: US 7,029,868 B2
(45) Date of Patent: Apr. 18, 2006

(54) CELL FUSION ASSAYS USING FLUORESCENCE RESONANCE ENERGY TRANSFER

(75) Inventors: Kathleen A. Sullivan, Springfield, NJ (US); Diana Benincasa, Elizabeth, NJ (US); Margaret A. Cascieri, East Windsor, NJ (US); Lyndon J. Mitnaul, Piscataway, NJ (US); Lin-Lin Shiao, Westfield, NJ (US); Michael R. Tota, Middletown, NJ (US)

(73) Assignee: Merck & Co., Inc., Rahway, NJ (US)

( * ) Notice: Subject to any disclaimer, the term of this patent is extended or adjusted under 35 U.S.C. 154(b) by 410 days.

(21) Appl. No.: 10/204,200

(22) PCT Filed: Feb. 13, 2001

(86) PCT No.: PCT/US01/04677

§ 371 (c)(1),
(2), (4) Date: Aug. 16, 2002

(87) PCT Pub. No.: WO01/60995

PCT Pub. Date: Aug. 23, 2001

(65) Prior Publication Data

US 2003/0036108 A1    Feb. 20, 2003

Related U.S. Application Data

(60) Provisional application No. 60/183,309, filed on Feb. 17, 2000.

(51) Int. Cl.
*C12Q 1/34* (2006.01)
*C12Q 1/00* (2006.01)
*C12N 5/00* (2006.01)
*C12N 15/02* (2006.01)
*C07H 19/04* (2006.01)

(52) U.S. Cl. .................. 435/18; 435/4; 435/325; 435/449; 435/346; 536/26.6

(58) Field of Classification Search ................ 435/18, 435/325, 235.1, 436, 449, 4, 346; 536/26.6
See application file for complete search history.

(56) References Cited

U.S. PATENT DOCUMENTS 5,741,657 A    4/1998   Tsien et al.
5,981,200 A    11/1999  Tsien et al.
6,031,094 A    2/2000   Tsien et al.

OTHER PUBLICATIONS

Cohen et al. Methodologies in the study of cell-cell fusion. Methods. vol. 16, No. 2, pp. 215-226, Oct. 1998.*
Pecheur et al. Peptides and membrane fusion: towards and understanding of the molecular mechanism of protein-induced fusion. Journal of Membrane Biology. vol. 167, pp. 1-17, Jan. 1999.*
Dutch et al. Membrane fusion promoted by increasing surface densities of the paramyxovirus F and HN proteins. J Virol. vol. 72, No. 10, pp. 7745-7753, Oct. 1998.*
Horvath et al. Biological activity of paramyxovirus fusion proteins: factors influencing formation of syncytia. J Virol. vol. 66, No. 7, pp. 4564-4569, Jul. 1992.*
Gravel et al. Interacting domains of the HN and F proteins of newcastle disease virus.☐☐J Virol. vol. 77, No. 20, pp. 11040-11049, Oct. 2003.*
Feng et al., "HIV-1 Entry Cofactor: Functional cDNA Cloning of a Seven-Transmembrane, G Protein-Coupled Receptor", Science, vol. 272, pp. 872-877 (May 1996).
Cocchi, et al., "Identification of RANTES, MIP-1α, and MIP-1β as the Major HIV-Suppresive Factors Produced by CD8+ T Cells", Science, vol. 270, pp. 1811-1815 (Dec. 1995).
Berger, "HIV entry and tropism: the chemokine receptor connection", AIDS, vol. 11, Suppl. A, pp. S3-S16 (1997).

(Continued)

*Primary Examiner*—Terry McKelvey
*Assistant Examiner*—Jennifer Dunston
(74) *Attorney, Agent, or Firm*—Joan E. Switzer; Joanne M. Giesser

(57) ABSTRACT

Methods of identifying inhibitors of the fusion of two types of cells, particularly when fusion is mediated by the interaction of a viral protein and such cellular proteins as CD4 and chemokine receptors, are disclosed. The methods are suitable for identifying substances that are useful for the treatment and prevention of viral diseases. Particularly preferred methods are useful for the identification of inhibitors of HIV-1 infection.

10 Claims, 8 Drawing Sheets

OTHER PUBLICATIONS

Rucker et al., "Utilization of Chemokine Receptors, Orphan Receptors, and Herpesvirus-Encoded Receptors by Diverse Human and Simian Immunodeficiency Viruses", Journal of Virology, vol. 71, No. 12, pp. 8999-9007 (1997).

Wyatt and Sodroski, "The HIV-1 Envelope Glycoproteins: Fusogens, Antigens, and Immunogens", Science, vol. 280, pp. 1884-1888 (Jun. 1998).

Zhang et al., "HIV-1 subtype and second-receptor use", Nature, vol. 383, p. 768 (Oct. 1996).

Connor et al., "Change in Coreceptor Use Correlates with Disease Progression in HIV-1-Infected Individuals", J. Exp. Med., vol. 185, No. 4, pp. 621-628 (Feb. 17, 1997).

Bjorndal et al., "Coreceptor Usage of Primary Human Immunodeficiency Virus Type 1 Isolates Varies According to Biological Phenotype", Journal of Virology, vol. 71, No. 10, pp. 7478-7487 (1997).

Scarlatti et al., "In vivo evolution of HIV-1 co-receptor usage and sensitivity to chemokine-mediated suppresion", Nature Medicine, vol. 3, No. 11, pp. 1259-1265 (Nov. 1997).

Bazan et al., "Patterns of CCR5, CXCR4, and CCR3 Usage by Envelope Glycoproteins from Human Immunodeficiency Virus Type 1 Primary Isolates", Journal of Virology, vol. 72, No. 5, pp. 4485-4491 (1998).

Nussbaum et al., "Fusogenic Mechanisms of Enveloped-Virus Glycoproteins Analyzed ay a Novel Recombinant Vaccinia Virus-Based Assay Quantitating Cell Fusion-Dependent Reproter Gene Activation", Journal of Virology, vol. 68, No. 9, pp. 5411-5422 (Sep. 1994).

Weiss et al., "Studies of HIV-1 envelope glycoprotein-mediated fusion using a simple fluorescence assay", AIDS, vol. 10, No. 3, pp. 241-246 (1996).

Litwin et al., Human Immunodeficiency Virus Type 1 Membrane Fusion Mediated by a Laboratory-Adapted Strain and a Primary Isolate Analyzed by Resonance Energy Transfer, Journal of Virology, vol. 70, pp. 6437-6441 (1996).

Zlokarnik et al., "Quantitation of Transcription and Clonal Selection of Single Living Cells with β-Lactamase as Reporter", Science, vol. 279, pp. 84-88 (Jan. 1998).

Clegg, "Fluorescence resonance energy transfer", Current Opinion in Biotechnology, vol. 6, pp. 103-110 (1995).

Berger et al., "Chemokine Receptors as HIV-1 Coreceptors: Roles in Viral Entry, Tropism, and Disease", Annu. Rev. Immunol., vol. 17, pp. 657-700 (1999).

Owman et al., "The leukotriene B4 receptor functions as a novel type of coreceptor mediating entry of primary HIV-1 isolates into CD4-positive cells", Proc. Natl. Acad. Sci. USA, vol. 95, pp. 9530-9534 (Aug.1998).

Samson et al., "ChemR23, a putative chemoattractant receptor , is expressed in monocyte-derived dendritic cells and macrophages and is a coreceptor for SIV and some primary HIV-1 strains", Eur. J. Immunol., vol. 28, pp. 1689-1700 (1998).

Albrecht et al., "Dual-Action Cephalosporins: Cephalosporin 3'-Quaternary Ammonium Quinolones", J. Med. Chem., vol. 34, pp. 669-675 (1991).

Cammack, "Human immunodeficiency virus type 1 entry and chemokine receptors: a new therapeutic target", Antiviral Chemistry & Chemotherapy, vol. 10, pp. 53-62 (1999).

McManus and Doms, "Fusion Mediated by the HIV-1 Envelope Protein", Subcellular Biochemistry, vol. 34: Fusion of Biological Membranes and Related Problems, pp. 457-481, New York (2000).

Sittampalam et al., "High-throughput screening: advances in assay technologies", Current Opinion in Chemical Biology, vol. 1, pp. 384-391 (1997).

Szollosi et al., "Application of Fluorescence Resonance Energy Transfer in the Clinical Laboratory: Routine and Research", Cytometry (Communications in Clinical Cyometry), vol. 34, pp. 159-179 (1998).

De Silva, et al., "Emerging fluorescence sensing technologies: From photophysical principles to cellular applications," Proc. Natl. Acad. Sci. USA, vol. 96, pp. 8336-8337 (Jul. 1999).

Mathis, "Probing Molecular Interactions with Homogeneous Techniques Based on Rare Earth Cryptates and Fluorescence Energy Transfer", Clinical Chemistry, vol. 41, No, 9, pp. 1391-1397 (1995).

Heery et al., "A signature motif in transcriptional co-activators mediates binding to nuclear receptors", Nature, vol. 387, pp. 733-736 (Jun. 1997).

Montminy, "Something new to hang your HAT on", Nature, vol. 387, pp. 654-655 (Jun. 1997).

Torchia et al., "The transcriptional co-activator p/CIP binds CBP and mediates nuclear-receptor function", Nature, vol. 387, pp. 677-684 (Jun. 1997).

* cited by examiner

```
   1 TCGCGCGTTT CGGTGATGAC GGTGAAAACC TCTGACACAT GCAGCTCCCG
  51 GAGACGGTCA CAGCTTGTCT GTAAGCGGAT GCCGGGAGCA GACAAGCCCG
 101 TCAGGGCGCG TCAGCGGGTG TTGGCGGGTG TCGGGGCTGG CTTAACTATG
 151 CGGCATCAGA GCAGATTGTA CTGAGAGTGC ACCATATGCG GTGTGAAATA
 201 CCGCACAGAT GCGTAAGGAG AAAATACCGC ATCAGATTGG CTATTGGCCA
 251 TTGCATACGT TGTATCCATA TCATAATATG TACATTTATA TTGGCTCATG
 301 TCCAACATTA CCGCCATGTT GACATTGATT ATTGACTAGT TATTAATAGT
 351 AATCAATTAC GGGGTCATTA GTTCATAGCC CATATATGGA GTTCCGCGTT
 401 ACATAACTTA CGGTAAATGG CCCGCCTGGC TGACCGCCCA ACGACCCCCG
 451 CCCATTGACG TCAATAATGA CGTATGTTCC CATAGTAACG CCAATAGGGA
 501 CTTTCCATTG ACGTCAATGG GTGGAGTATT TACGGTAAAC TGCCCACTTG
 551 GCAGTACATC AAGTGTATCA TATGCCAAGT ACGCCCCCTA TTGACGTCAA
 601 TGACGGTAAA TGGCCCGCCT GGCATTATGC CCAGTACATG ACCTTATGGG
 651 ACTTTCCTAC TTGGCAGTAC ATCTACGTAT TAGTCATCGC TATTACCATG
 701 GTGATGCGGT TTTGGCAGTA CATCAATGGG CGTGGATAGC GGTTTGACTC
 751 ACGGGGATTT CCAAGTCTCC ACCCCATTGA CGTCAATGGG AGTTTGTTTT
 801 GGCACCAAAA TCAACGGGAC TTTCCAAAAT GTCGTAACAA CTCCGCCCCA
 851 TTGACGCAAA TGGGCGGTAG GCGTGTACGG TGGGAGGTCT ATATAAGCAG
 901 AGCTCGTTTA GTGAACCGTC AGATCGCCTG GAGACGCCAT CCACGCTGTT
 951 TTGACCTCCA TAGAAGACAC CGGGACCGAT CCAGCCTCCG CGGCCGGGAA
1001 CGGTGCATTG GAACGCGGAT TCCCCGTGCC AAGAGTGACG TAAGTACCGC
1051 CTATAGAGTC TATAGGCCCA CCCCCTTGGC TTCTTATGCA TGCTATACTG
1101 TTTTTGGCTT GGGGTCTATA CACCCCGCT TCCTCATGTT ATAGGTGATG
1151 GTATAGCTTA GCCTATAGGT GTGGGTTATT GACCATTATT GACCACTCCC
```

FIG.5A

```
1201 CTATTGGTGA CGATACTTTC CATTACTAAT CCATAACATG GCTCTTTGCC
1251 ACAACTCTCT TTATTGGCTA TATGCCAATA CACTGTCCTT CAGAGACTGA
1301 CACGGACTCT GTATTTTTAC AGGATGGGGT CTCATTTATT ATTTACAAAT
1351 TCACATATAC AACACCACCG TCCCCAGTGC CCGCAGTTTT TATTAAACAT
1401 AACGTGGGAT CTCCACGCGA ATCTCGGGTA CGTGTTCCGG ACATGGGCTC
1451 TTCTCCGGTA GCGGCGGAGC TTCTACATCC GAGCCCTGCT CCCATGCCTC
1501 CAGCGACTCA TGGTCGCTCG GCAGCTCCTT GCTCCTAACA GTGGAGGCCA
1551 GACTTAGGCA CAGCACGATG CCCACCACCA CCAGTGTGCC GCACAAGGCC
1601 GTGGCGGTAG GGTATGTGTC TGAAAATGAG CTCGGGGAGC GGGCTTGCAC
1651 CGCTGACGCA TTTGGAAGAC TTAAGGCAGC GGCAGAAGAA GATGCAGGCA
1701 GCTGAG77GT TGTGTTCTGA TAAGAGTCAG AGGTAACTCC CGTTGCGGTG
1751 CTGTTAACGG TGGAGGGCAG TGTAGTCTGA GCAGTACTCG TTGCTGCCGC
1801 GCGCGCCACC AGACATAATA GCTGACAGAC TAACAGACTG TTCCTTTCCA
1851 TGGGTCTTTT CTGCAGTCAC CGTCCTTAG  ATCTGCTGTG CCTTCTAGTT
1901 GCCAGCCATC TGTTGTTTGC CCCTCCCCCG TGCCTTCCTT GACCCTGGAA
1951 GGTGCCACTC CCACTGTCCT TTCCTAATAA AATGAGGAAA TTGCATCGCA
2001 TTGTCTGAGT AGGTGTCATT CTATTCTGGG GGGTGGGGTG GGGCAGCACA
2051 GCAAGGGGGA GGATTGGGAA GACAATAGCA GGCATGCTGG GGATGCGGTG
2101 GGCTCTATGG GTACCCAGGT GCTGAAGAAT TGACCCGGTT CCTCCTGGGC
2151 CAGAAAGAAG CAGGCACATC CCCTTCTCTG TGACACACCC TGTCCACGCC
2201 CCTGGTTCTT AGTTCCAGCC CCACTCATAG GACACTCATA GCTCAGGAGG
2251 GCTCCGCCTT CAATCCCACC CGCTAAAGTA CTTGGAGCGG TCTCTCCCTC
2301 CCTCATCAGC CCACCAAACC AAACCTAGCC TCCAAGAGTG GGAAGAAATT
2351 AAAGCAAGAT AGGCTATTAA GTGCAGAGGG AGAGAAAATG CCTCCAACAT
2401 GTGAGGAAGT AATGAGAGAA ATCATAGAAT TTCTTCCGCT TCCTCGCTCA
```

FIG.5B

```
2451 CTGACTCGCT GCGCTCGGTC GTTCGGCTGC GGCGAGCGGT ATCAGCTCAC
2501 TCAAAGGCGG TAATACGGTT ATCCACAGAA TCAGGGGATA ACGCAGGAAA
2551 GAACATGTGA GCAAAAGGCC AGCAAAAGGC CAGGAACCGT AAAAAGGCCG
2601 CGTTGCTGGC GTTTTTCCAT AGGCTCCGCC CCCCTGACGA GCATCACAAA
2651 AATCGACGCT CAAGTCAGAG GTGGCGAAAC CCGACAGGAC TATAAAGATA
2701 CCAGGCGTTT CCCCCTGGAA GCTCCCTCGT GCGCTCTCCT GTTCCGACCC
2751 TGCCGCTTAC CGGATACCTG TCCGCCTTTC TCCCTTCGGG AAGCGTGGCG
2801 CTTTCTCAAT GCTCACGCTG TAGGTATCTC AGTTCGGTGT AGGTCGTTCG
2851 CTCCAAGCTG GGCTGTGTGC ACGAACCCCC CGTTCAGCCC GACCGCTGCG
2901 CCTTATCCGG TAACTATCGT CTTGAGTCCA ACCCGGTAAG ACACGACTTA
2951 TCGCCACTGG CAGCAGCCAC TGGTAACAGG ATTAGCAGAG CGAGGTATGT
3001 AGGCGGTGCT ACAGAGTTCT TGAAGTGGTG GCCTAACTAC GGCTACACTA
3051 GAAGGACAGT ATTTGGTATC TGCGCTCTGC TGAAGCCAGT TACCTTCGGA
3101 AAAAGAGTTG GTAGCTCTTG ATCCGGCAAA CAAACCACCG CTGGTAGCGG
3151 TGGTTTTTTT GTTTGCAAGC AGCAGATTAC GCGCAGAAAA AAAGGATCTC
3201 AAGAAGATCC TTTGATCTTT TCTACGGGGT CTGACGCTCA GTGGAACGAA
3251 AACTCACGTT AAGGGATTTT GGTCATGAGA TTATCAAAAA GGATCTTCAC
3301 CTAGATCCTT TTAAATTAAA AATGAAGTTT TAAATCAATC TAAAGTATAT
3351 ATGAGTAAAC TTGGTCTGAC AGTTACCAAT GCTTAATCAG TGAGGCACCT
3401 ATCTCAGCGA TCTGTCTATT TCGTTCATCC ATAGTTGCCT GACTCCGGGG
3451 GGGGGGGGCG CTGAGGTCTG CCTCGTGAAG AAGGTGTTGC TGACTCATAC
3501 CAGGCCTGAA TCGCCCCATC ATCCAGCCAG AAAGTGAGGG AGCCACGGTT
3551 GATGAGAGCT TTGTTGTAGG TGGACCAGTT GGTGATTTTG AACTTTTGCT
3601 TTGCCACGGA ACGGTCTGCG TTGTCGGGAA GATGCGTGAT CTGATCCTTC
3651 AACTCAGCAA AAGTTCGATT TATTCAACAA AGCCGCCGTC CCGTCAAGTC
```

FIG.5C

```
3701 AGCGTAATGC TCTGCCAGTG TTACAACCAA TTAACCAATT CTGATTAGAA
3751 AAACTCATCG AGCATCAAAT GAAACTGCAA TTTATTCATA TCAGGATTAT
3801 CAATACCATA TTTTTGAAAA AGCCGTTTCT GTAATGAAGG AGAAAACTCA
3851 CCGAGGCAGT TCCATAGGAT GGCAAGATCC TGGTATCGGT CTGCGATTCC
3901 GACTCGTCCA ACATCAATAC AACCTATTAA TTTCCCCTCG TCAAAAATAA
3951 GGTTATCAAG TGAGAAATCA CCATGAGTGA CGACTGAATC CGGTGAGAAT
4001 GGCAAAAGCT TATGCATTTC TTTCCAGACT TGTTCAACAG GCCAGCCATT
4051 ACGCTCGTCA TCAAAATCAC TCGCATCAAC CAAACCGTTA TTCATTCGTG
4101 ATTGCGCCTG AGCGAGACGA AATACGCGAT CGCTGTTAAA AGGACAATTA
4151 CAAACAGGAA TCGAATGCAA CCGGCGCAGG AACACTGCCA GCGCATCAAC
4201 AATATTTTCA CCTGAATCAG GATATTCTTC TAATACCTGG AATGCTGTTT
4251 TCCCGGGGAT CGCAGTGGTG AGTAACCATG CATCATCAGG AGTACGGATA
4301 AAATGCTTGA TGGTCGGAAG AGGCATAAAT TCCGTCAGCC AGTTTAGTCT
4351 GACCATCTCA TCTGTAACAT CATTGGCAAC GCTACCTTTG CCATGTTTCA
4401 GAAACAACTC TGGCGCATCG GGCTTCCCAT ACAATCGATA GATTGTCGCA
4451 CCTGATTGCC CGACATTATC GCGAGCCCAT TTATACCCAT ATAAATCAGC
4501 ATCCATGTTG GAATTTAATC GCGGCCTCGA GCAAGACGTT TCCCGTTGAA
4551 TATGGCTCAT AACACCCCTT GTATTACTGT TTATGTAAGC AGACAGTTTT
4601 ATTGTTCATG ATGATATATT TTTATCTTGT GCAATGTAAC ATCAGAGATT
4651 TTGAGACACA ACGTGGCTTT CCCCCCCCCC CCATTATTGA AGCATTTATC
4701 AGGGTTATTG TCTCATGAGC GGATACATAT TTGAATGTAT TTAGAAAAAT
4751 AAACAAATAG GGGTTCCGCG CACATTTCCC CGAAAAGTGC CACCTGACGT
4801 CTAAGAAACC ATTATTATCA TGACATTAAC CTATAAAAAT AGGCGTATCA
4851 CGAGGCCCTT TCGTC
```

FIG.5D

CELL FUSION ASSAYS USING FLUORESCENCE RESONANCE ENERGY TRANSFER

CROSS-REFERENCE TO RELATED APPLICATIONS

This application is a 371 of PCT/US 01/04677, filed Feb. 13, 2001, which claims priority to U.S. Provisional Application No. 60/183,309, filed Feb. 17, 2000.

STATEMENT REGARDING FEDERALLY-SPONSORED R&D

Not applicable.

REFERENCE TO MICROFICHE APPENDIX

Not applicable.

FIELD OF THE INVENTION

The present invention is directed to methods of using fluorescence resonance energy transfer to assay for the fusion of cells. Such methods are useful for the identification of substances that can inhibit such fusion. In particular, such methods are useful for the identification of substances that are capable of inhibiting the fusion of certain viruses, e.g., HIV-1, with their target cells.

BACKGROUND OF THE INVENTION

Chemokines are a large family of proteins having a single polypeptide chain of about 70–100 amino acids that act through G-protein coupled receptors to regulate a variety of biological processes such as the recruitment of immune cells to the site of inflammation, angiogenesis, hematopoiesis, and organogenesis. The name "chemokine" is derived from the words "chemoattractant" and "cytokine" and stems from the observation that most members of the family have leukocyte chemoattractant and cytokine-like activity. The primary function of chemokines is thought to be as regulators of the processes of leukocyte trafficking during immunity and inflammation. More than 50 members of the chemokine family are known (Wolpe & Cerami, 1989, FASEB J. 3:2565–2573; Baggiolini et al., 1994, Adv. Immunol. 55:97–179; Locati & Murphy, 1999, Ann. Rev. Med. 50:425–440; Luster, 1998, New Eng. J. Med. 338:436–445).

Chemokines have been divided into subfamilies based upon the number and spacing of conserved cysteine residues. The CC and CXC subfamilies have four cysteines, of which the first two are either adjacent (the CC subfamily) or separated by a single amino acid (the CXC subfamily). Both of these subfamilies have multiple members, which carry out their biological roles through interaction with a wide variety of chemokine receptors. In addition, there are two additional chemokine families: the C family, with no intervening amino acids, and the CXXXC family with three intervening amino acids.

There are at least 15 types of chemokine receptors, with each type of receptor generally being capable of binding to a particular subfamily of chemokines. The names of the receptors reflect this subfamily-restricted binding specificity. Thus, the receptors that bind CXC chemokines are known as the CXCRs; those receptors that bind CC chemokines are known as CCRs. The general subfamily-specific name is followed by a number, reflecting the order of discovery of a particular receptor. Thus, CXCR4 was the fourth receptor found that was specific for the CXC subfamily of chemokines. Chemokine receptors belong to the large class of rhodopsin-like, 7-transmembrane (7TM), G-protein coupled receptors (GPCRs). They are generally coupled to Gi-type proteins (Murphy, 1994, Ann. Rev. Immunol. 12:593–633; Murphy, 1996, Cytokine Growth Factor Rev. 7:47–64; Yoshie et al., 1997, J. Leukocyte Biol. 62:634–644).

An important development in chemokine research occurred with the discovery that certain chemokines could suppress HIV-1 virus infection in vitro. This effect was determined to be due to blockage of the interaction of the virus's envelope glycoprotein (Env) with certain chemokine receptors. The primary receptor for all strains of HIV-1 is CD4, a membrane protein found on T cells and certain other cells, but strain-specific chemokine receptors are also required as coreceptors. The interaction of Env, CD4, and the chemokine receptor results in the fusion of the viral and target cell membranes (Feng et al., 1996, Science 272: 872–877; Cocchi et al., 1995, Science 270:1811–1815; Berger, 1997, AIDS 11(Suppl. A):S3–16; Rucker et al., 1997, J. Virol. 71:8999–9007; Wyatt & Sodroski, 1998, Science 280:1884–1888).

The most widely used chemokine coreceptors for HIV-1 are CCR5 and CXCR4. Virtually all primary HIV-1 isolates use either CXCR4, CCR5, or both (Zhang et al, 1996, Nature 383:768; Connor et al., 1997, J. Exp. Med. 185:621–628; Bjorndal et al., 1997, J. Virol. 71:7478–7487; Scarlatti et al., 1997, Nature Med. 3:1259–1265; Bazan et al., 1998, J. Virol. 72:4485–4491). There is a curious and as yet incompletely explained tropism to HIV-1 isolates. CCR5-specific strains are associated with early infection and the period of clinical latency while CXCR4-specific strains are associated with later stages of infection that include immune system collapse and AIDS. The earlier strains are able to infect primary macrophages in vitro while the later strains are able to infect T cell lines. This cellular tropism is understood to be due to the different patterns of chemokine receptor expression in the two target cell types; macrophages express CCR5 while T cells express CXCR4. In general, HIV-1 tropism can be explained by the ability of an HIV-1 isolate's Env to recognize a particular chemokine receptor and by the expression patterns of these chemokine receptors on CD4+ target cells. In fact, tropism has been re-defined based upon the usage of CCR5 (R5 tropic virus), CXCR4 (X4 tropic virus), or both CCR5 and CXCR4 (R5x4). Although helpful, this simplified picture is subject to occasional complications. For example, macrophages express CXCR4 in addition to CCR5. The block to X4 tropic virus in macrophages occurs post entry. Although CCR5 and CXCR4 are the principal coreceptors utilized in vivo, many other chemokine receptors and related orphan receptors also have HIV-1 coreceptor activity in vitro, including CX3CR1, CCR8, CCR2, CCR3, STRL33/BONZO, GPR1, GPR15, and APJ (Berger, 1997, AIDS 11 (Suppl. A):S3–16; Rucker et al., 1997, J. Virol. 71:8999–9007).

The role of CCR5 in the pathogenesis of HIV-1 infection and the development of AIDS has been clearly demonstrated. A mutant allele with a 32 base pair deletion that results in a truncated, inactive receptor (CCR5 d32) is found in homozygous form about 20-fold less frequently in HIV-1 infected people than in the general population, indicating a substantial protective effect (Liu et al., 1996, Cell 86:367–377; Dean et al., 1996, Science 273:1856–1862). Other polymorphisms in chemokines or their receptors have been found to be associated with various levels of resistance to HIV-1 pathogenesis. Of special note is a polymorphism in the 3' untranslated region of SDF-1 mRNA. SDF-1 is a chemokine ligand of CXCR4 (Winkler et al., 1998, Science 279:389–393). In addition to molecular epidemiology studies, much in vitro evidence strongly suggests that chemokine receptors play a role in HIV-1 pathogenesis. For example, the CCR5 ligands MIP-1α, MIP-1β, and RANTES are able to suppress HIV-1 replication in certain cultured cells (Cocchi et al., 1995, Science 270:1811–1815). Furthermore, a low molecular weight bicyclam compound, AMD3100, inhibits HIV-1 replication in SCID-hu mice (Datema et al., 1996, Antimicrob. Agents Chemother. 40:750–754). AMD3100 acts by blocking virus interaction with the CXCR4 coreceptor (Schols et al., 1997, J. Exp. Med. 186:1383–1388).

Since chemokine receptors are involved in HUV-1 pathogenesis, it is of great interest to identify substances that can inhibit the interaction of HIV-1 Env proteins and chemokine coreceptors. However, to date, satisfactory methods of identifying such inhibitors are lacking.

Nussbaum et al., 1994, J. Virol. 68:5411–5422 and Feng et al., 1996, Science 272:872–877 disclosed a system in which a first cell was infected with a vaccinia virus encoding an HIV envelope protein as well as bacteriophage T7 RNA polymerase. A second cell expressed CD4, a chemokine receptor, and the E. coli LacZ gene under the control of a T7 promoter. Upon fusion of the two cells, the T7 RNA polymerase from the first cell transcribed the LacZ reporter gene from the second cell and the activity of the product of the reporter gene was measured. Inhibitors of HIV fusion were identified by their ability to suppress readout from the reporter. This system has many disadvantages: generally, hours must pass before readout from the reporter occurs; the use of vaccinia virus requires Class 2 biosafety conditions; agents which block viral assembly and replication, such as araC or rifamycin, must be used; and, because the assay depends on the transcriptional activity of the T7 promoter, it will identify inhibitors of transcription in general, irrespective of whether such inhibitors affect fusion.

Several assays based upon fluorescence have been developed. Weiss et al., 1996, AIDS 10:241–246 labeled lymphocytes (cells that grow in suspension) with intracellular fluorescent dyes and mixed the labeled lymphocytes with unlabeled adherent cells under conditions where fusion could occur. The occurrence of fusion was monitored by scanning microscopic fields for the presence of fluorescent adherent cells. This assay did not make use of fluorescence resonance energy transfer and suffered from the drawback that the two cell types used must be morphologically distinct. Also, the assay is difficult to quantitate.

A similar assay was developed in which the two cells to be fused were labeled with two different fluorescent dyes, with the dyes having overlapping emission and excitation spectra (Litwin et al., 1996, J. Virol. 70:6437–6441 (Litwin); International Patent Publication WO 96/41020). The first and second dyes are chosen so that the emission spectrum of the first overlaps the absorption spectrum of the second. In the absence of fusion between the two cells, little fluorescence resonance energy transfer (FRET) will be observed since the two dyes are not likely to be physically close to one another. When the two cells are mixed under conditions such that they fuse, however, the two dyes are brought into close proximity within the fused membranes, thus allowing FRET between the two dyes to occur. If the two cells are mixed in the presence of an inhibitor of fusion, little or no FRET will be observed. Screening a collection of compounds for those compounds capable of diminishing or preventing FRET will identify compounds that are inhibitors of fusion. The assays described in Litwin and International Patent Publication WO 96/41020 require the use of two physically separate dyes since a different dye must be incorporated in each cell's membrane. Also, Litwin and International Patent Publication WO 96/41020 do not disclose the importance of chemokine receptors in the fusion process. Thus, the success of the methods described in Litwin and International Patent Publication WO 96/41020 depends on the chance selection of a cell type that coexpresses CD4 and an appropriate chemokine receptor. In addition, this assay requires the separate labeling of two different cell types, each with a different fluorescent dye.

An extremely sensitive assay for studying signal transduction that is based on FRET is disclosed in Zlokarnik et al., 1998, Science 279:84–88 (Zlokarnik) and also in U.S. Pat. No. 5,741,657. The assay disclosed in Zlokarnik and U.S. Pat. No. 5,741,657 is designed for the study of transcriptional activation that arises as a result of intracellular signaling pathways that are activated by ligand-receptor interactions. The assay employs a plasmid encoding β-lactamase under the control of an inducible promoter. This plasmid is transfected into cells together with a plasmid encoding a receptor for which it is desired to identify agonists. The inducible promoter on the β-lactamase is chosen so that it responds to at least one intracellular signal that is generated when an agonist binds to the receptor. Thus, following such binding of agonist to receptor, the level of β-lactamase in the transfected cells increases. This increase in β-lactamase is made measurable by treating the cells with a cell-permeable dye that is a substrate for β-lactamase. The dye contains two fluorescent moieties. In the intact dye, the two fluorescent moieties are close enough to one another that FRET can take place between them. Following cleavage of the dye into two parts by β-lactamase, the two fluorescent moieties are located on different parts, and thus can diffuse apart. This increases the distance between the flourescent moieties, decreasing the amount of FRET that can occur between them. It is this decrease in FRET that is measured in the assay. Zlokarnik used this assay to identify inhibitors of the $M_1$ muscarinic receptor. Zlokamik did not disclose the use of this assay to study membrane fusion in general and the interaction of HIV-1 and target cells in particular.

SUMMARY OF THE INVENTION

The present invention is directed to methods of identifying inhibitors of the fusion of two types of cells, one of which contains the enzyme β-lactamase and the other of which contains a fluorescent substrate of β-lactamase. The substrate is a compound comprising two moieties that are connected by a linker that is susceptible to cleavage by β-lactamase. Each moiety is independently fluorescent and the emission spectrum of one moiety overlaps the absorption spectrum of the other moiety. The molecular configuration of the substrate is such that, when the linker is intact, fluorescence resonance energy transfer (FRET) can occur between the two fluorescent moieties. When the linker has been cleaved by β-lactamase, the two moieties are no longer physically linked and can thus diffuse apart. This results in FRET being either abolished or greatly diminished.

In the absence of fusion between the two cells, when the cytoplasms of the two cells are separate, FRET will be observed since the linker of the fluorescent substrate will be intact. After fusion, when the two cytoplasms have mixed, β-lactamase from one cell will cleave the substrate from the other cell, diminishing or abolishing FRET. Thus, the measurement of FRET can serve as a measure of the amount of fusion that has occurred between the two types of cells.

In a version of the method, the two cell types are adherent cells and suspension cells. The suspension cells contain β-lactamase while the adherent cells do not. The suspension cells are overlayed on a lawn of adherent cells under conditions and for a time suitable for the occurrence of fusion between the two types of cells. After a suitable time, any unfused suspension cells are washed away, leaving a lawn of fused suspension and adherent cells, plus any unfused adherent cells. This lawn is then exposed to the substrate of β-lactamase for a time and under conditions such that the substrate enters the cytoplasms of the fused suspension and adherent cells and any unfused adherent cells. If fusion has occurred, the cytoplasm of the fused suspension and adherent cells will contain β-lactamase from the suspension cells. This β-lactamase will cleave the linker of the substrate, abolishing or diminishing FRET from the substrate. If fusion has not occurred, the linker in the substrate will not be cleaved, since no β-lactamase will have been delivered by the suspension cells, and FRET will occur.

The methods can be used to monitor fusion that is dependent on the presence of certain proteins in the cytoplasmic membranes of the two cell types. In a particular embodiment, the method is used to identify inhibitors of fusion mediated by an HIV-1 Env protein in the cytoplasmic membrane of one cell and CD4 and a chemokine receptor in the cytoplasmic membrane of the other cell. In this embodiment, the two cells serve as models for the fusion process that occurs during HIV-1 infection. Accordingly, inhibitors identified using the present invention are expected to be useful as drugs to prevent or ameliorate the effects of HIV-1 infection and AIDS.

BRIEF DESCRIPTION OF THE DRAWINGS

FIGS. 5A–D shows the DNA sequence of the expression vector pV1Jneo (SEQ.ID.NO.:1).

DETAILED DESCRIPTION OF THE INVENTION

Figure 1:
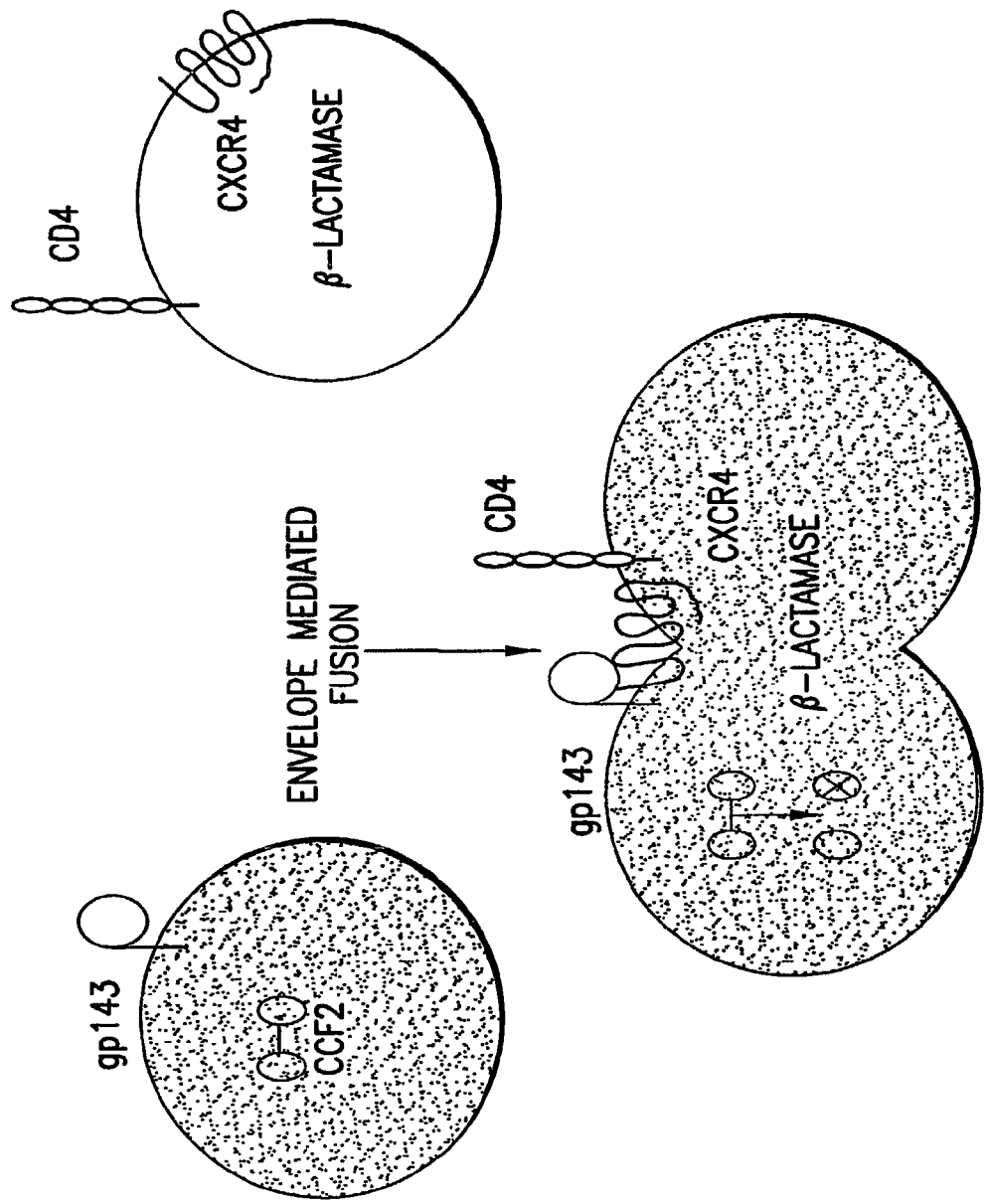
FIG. 1 shows the general features of the present invention as practiced in an embodiment where fusion is mediated by a viral protein on the cytoplasmic membrane of a first cell and two cell surface proteins on the cytoplasmic membrane of a second cell.

The present invention provides a method for monitoring the fusion of two cell types via the measurement of fluorescence resonance energy transfer (FRET). FRET is a process in which energy is transferred from an excited donor fluorescent reagent to an acceptor fluorescent reagent by means of intermolecular long-range dipole-dipole coupling. FRET typically occurs over distances of about 10 Å to 100 Å and requires that the emission spectrum of the donor reagent and the absorbance spectrum of the acceptor reagent overlap adequately and that the quantum yield of the donor and the absorption coefficient of the acceptor be sufficiently high. Ideally, the donor has a high fluorescence quantum yield (preferably, approaching 100%) and the acceptor has a large extinction coefficient at wavelengths coinciding with the emission wavelengths of the donor. In addition, the transition dipoles of the donor and acceptor fluorescent reagents must be properly oriented relative to one another. For a review of FRET and its applications in biological systems, see Clegg, 1995, Current Opinions in Biotechnology 6:103–110.

In its broadest aspect, the present invention provides a method for monitoring the fusion of two cell types via the measurement of FRET where only one of the cell types expresses β-lactamase and FRET is measured from a fluorescent substrate of β-lactamase where the substrate is a compound comprising two fluorescent moieties that are connected by a linker that is susceptible to cleavage by β-lactamase and the two fluorescent moieties are selected such that the emission spectrum of one overlaps the absorption spectrum of the other. When the two cell types are unfused, FRET occurs between the two fluorescent moieties of the substrate. When the two cell types are fused, the fluorescent substrate is cleaved by β-lactamase, separating the two fluorescent moieties and diminishing or abolishing FRET. Thus, the measurement of the amount of FRET gives an indication of the amount of fusion that has occurred.

Accordingly, the present invention provides a method for determining the amount of fusion that occurs between two cells via the measurement of fluorescence resonance energy transfer (FRET) comprising:

(a) providing a first cell that expresses β-lactamase;

(b) providing a second cell that does not express β-lactamase but contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where FRET can occur when the linker is intact but does not occur when the linker has been cleaved;

(c) measuring the amount of FRET from the substrate in the second cell in the absence of fusion between the first and second cells;

(d) bringing the first and second cells into contact under conditions such that fusion occurs;

(e) measuring the amount of FRET from the substrate after fusion has occurred;

where, if the amount of FRET measured in step (c) is different from and greater than the amount of FRET measured in step (e), then fusion has occurred, with larger differences indicating greater amounts of fusion.

The present invention further includes a method for identifying inhibitors of the fusion of a first and a second cell comprising:

(a) providing a first cell that expresses β-lactamase;

(b) providing a second cell that does not express β-lactamase but contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved;

(c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance;

(d) measuring the amount of FRET in step (c) in the presence and in the absence of the substance;

where if the amount of FRET is greater in the presence of the substance than in the absence of the substance, then the substance is an inhibitor of the fusion of the first and the second cells.

The present invention may also be practiced in such a way that, rather than using a second cell that contains the fluorescent substrate of β-lactamase, the substrate is added to the fused first and second cells after fusion takes place. Such a version of the invention is especially suitable where the first cell is a cell that grows in suspension culture (referred to herein as a "suspension cell") and the second cell is a cell that grows as adherent cells in a monolayer on a tissue culture plate (referred to herein as an "adherent cell").

Accordingly, the present invention provides a method of identifying an inhibitor of the fusion of a first and a second cell comprising:

(a) providing a first cell that expresses β-lactamase where the first cell is a suspension cell;

(b) providing a second cell that does not express β-lactamase where the second cell is an adherent cell;

(c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance;

(d) washing away any unfused first cells;

(e) exposing the fused cells to a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved under conditions and for a sufficient time such that the substrate is taken up into the cytoplasm of the fused cells and into the cytoplasm of any unfused adherent cells;

(f) measuring the amount of FRET from the substrate in the fused cells;

where if the amount of FRET is greater in the presence of the substance than in the absence of the substance, then the substance is an inhibitor of the fusion of the first and the second cells.

In particular embodiments, fusion is mediated by proteins that are found in or on the cytoplasmic membranes of the cells. By "mediated" is meant that fusion will not occur to a significant extent in the absence of the protein. The proteins may be (a) a viral protein in or on the cytoplasmic membrane of one type of cell where the viral protein normally mediates fusion of the virus with its target cells during the usual course of viral infection; and (b) a protein or proteins from the target cell that is recognized by the viral protein during the course of natural infection of the target cell by the virus. In these embodiments, the methods of the present invention are useful to identify inhibitors of fusion that are substances that can treat or prevent viral disease.

FIG. 1 is a schematic illustration of an embodiment of the present invention where fusion is mediated by the presence of an HIV-1 envelope glycoprotein (gp143) in the cytoplasmic membrane of a first cell and the proteins CD4 and CXCR4 in the cytoplasmic membrane of a second cell. The fluorescent substrate CCF2 (described herein) is present in the first cell while the enzyme β-lactamase is present in the second cell. The "X" over the acceptor fluorescent moiety of CCF2 in the fused cells indicates that FRET has been abolished or diminished.

The present invention includes a method for identifying inhibitors of the fusion of a first and a second cell comprising:

(a) providing a first cell that expresses β-lactamase where the first cell also expresses CD4 and a chemokine receptor;

(b) providing a second cell that does not express β-lactamase but contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved and where the second cell also expresses a viral protein that mediates fusion;

(c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance;

(d) measuring the amount of FRET in step (c) in the presence and in the absence of the substance;

where if the amount of FRET is greater in the presence of the substance than in the absence of the substance, then the substance is an inhibitor of the fusion of the first and the second cells.

The present invention includes a method for identifying inhibitors of the fusion of a first and a second cell comprising:

(a) providing a first cell that expresses β-lactamase where the first cell also expresses a viral protein that mediates fusion;

(b) providing a second cell that does not express β-lactamase but contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved and where the second cell also expresses CD4 and a chemokine receptor;

(c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance;

(d) measuring the amount of FRET in step (c) in the presence and in the absence of the substance;

where if the amount of FRET is greater in the presence of the substance than in the absence of the substance, then the substance is an inhibitor of the fusion of the first and the second cells.

The present invention provides a method of identifying an inhibitor of the fusion of a first cell and a second cell comprising:

(a) providing a first cell that expresses β-lactamase where the first cell is a suspension cell that also expresses CD4 and a chemokine receptor;

(b) providing a second cell that does not express β-lactamase where the second cell is an adherent cell that expresses a viral protein that mediates fusion of the first and the second cells;

(c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance;

(d) washing away any unfused first cells;

(e) exposing the fused cells to a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved under conditions and for a sufficient time such that the substrate is taken up into the cytoplasm of the fused cells and the cytoplasm of any unfused adherent cells;

(f) measuring the amount of FRET from the substrate in the fused cells or any unfused adherent cells;

where if the amount of FRET is greater in the presence of the substance than in the absence of the substance, then the substance is an inhibitor of the fusion of the first and the second cells.

In certain embodiments of the present invention the proteins or polypeptides that mediate fusion (e.g., CD4, Env, chemokine receptor) are expressed naturally (i.e., without human intervention) by the cells. In other embodiments, the proteins or polypeptides that mediate fusion are expressed recombinantly in the cells. Recombinant expression may be accomplished by transfection methods that are well known in the art. The methods of the present invention can be carried out with cells that have been transiently or stably transfected with an expression vector encoding a protein or polypeptide that mediates fusion. Transfection is meant to include any method known in the art. For example, transfection includes calcium phosphate or calcium chloride mediated transfection, lipofection, infection with a retroviral construct, and electroporation. When using cells that have been transiently transfected, it is often preferable to fuse such cells within the first 72 hours, preferably about 24 hours, after transfection.

In particular embodiments, it may be desirable to express an HIV-1 Env protein under the control of an inducible promoter so as to overcome any potential toxicity problems associated with overexpressing Env proteins. Suitable inducible promoters are known in the art.

In particular embodiments, the chemokine receptor is a human chemokine receptor. A variety of chemokine receptors can be used in the present invention. Table 1, page 663 and accompanying text of Berger et al., 1999, Ann. Rev. Immunol. 17:657–700 lists many chemokine receptors that are suitable. Among these are: CCR5, CXCR4, CX3CR1, CCR8, CCR2B, CCR9, CCR3, STRL33/BONZO, GPR15/BOB, and APJ. BLTR, the leukotriene B4 receptor, has been reported to have HIV-1 coreceptor activity (Owman et al., 1998, Proc. Natl. Acad. Sci. USA 95:9530–9534) as has the orphan receptor Chem R23 (Samson et al., 1998, Eur. J. Immunol. 28:1689–1700). Therefore, these receptors are also suitable.

While the proteins that mediate fusion that are suitable for use in the present invention are usually human proteins, it may be suitable to use proteins of other species as well. For example, murine CXCR4 can function as a coreceptor for certain HIV-1 strains and would therefore be suitable for use in methods to identify inhibitors of those strains. However, murine CCR5 does not function as a coreceptor and therefore would not be suitable.

While the above-described methods of identifying inhibitors of fusion are, for the sake of clarity of explanation, explicitly directed to testing whether "a" substance is an inhibitor of fusion, it will be clear to one skilled in the art that such methods can be adapted to test collections of substances (e.g., combinatorial libraries, phage display libraries, collections of natural products, or the products of a medicinal chemistry lead optimization program) to determine whether any members of such collections are inhibitors of fusion. Accordingly, the use of collections of substances, or subsets of such collections, or individual members of such collections, as the substance in the above-described methods is within the scope of the present invention.

The methods of the present invention are generally described as making use of "a" first cell and "a" second cell. The use of the singular article is for the sake of clarity of explanation. Those skilled in the art will understand that the methods will usually be practiced with a plurality, often thousands or even millions, of first cells and second cells, as when cells are grown in tissue culture and then used in the methods.

In certain embodiments of the present invention, the cells used do not naturally express a chemokine receptor. Instead, DNA encoding a chemokine receptor is transfected into cells in order to express the chemokine receptor on the surface of the cells. DNA encoding chemokine receptors can be obtained by methods well known in the art. For example, a cDNA fragment encoding a chemokine receptor can be isolated from a cDNA library by using the polymerase chain reaction (PCR) employing suitable primer pairs. Such primer pairs can be selected based upon the known DNA sequence of the chemokine receptor it is desired to obtain. For example, Randolph et al., 1999, Science 286:2159–2162, at page 2162, disclose the use of the following primers to clone cDNA encoding CCR7 via PCR from murine $T_H1$ cells:

5'-GAGACTCGAGAGAGCACCATGGACCCAGG-3' (SEQ.ID.NO.:2) and

5'-GAGAGAATTCCTACGGGGAGAAGGTTGTGG-3' (SEQ.ID.NO.:3).

In a similar manner, one skilled in the art could use published human chemokine receptor sequences and published studies of human chemokine receptor expression (to select the appropriate tissues from which to make cDNA libraries) in order to obtain DNA encoding human chemokine receptors. The following publications may be of use in this regard:

GenBank accession number AF005058 (human CXCR4)

GenBank accession number D49919 (human CCR2)

Kato et al., 1999, Genes Immun. 1:97–104 and GenBank accession number AB023887 (human CCR3)

Kato et al., 1999, Genes Immun. 1:97–104 and GenBank accession number AB023888 (human CCR4)

Kato et al., 1999, Genes Immun. 1:97–104 and GenBank accession number AB023889 (human CCR4)

Mumidi et al., 1997, J. Biol. Chem. 272:30662–30671 and GenBank accession number HSCCR5AB2 (human CCR5)

Baba et al., 1997, J. Biol. Chem. 272:14893–14898 and GenBank accession number HSU45984 (human CCR6)

Tiffany et al., 1997, J. Exp. Med. 186:165–170 and GenBank accession number HSU45983 (human CCR8)

Zaballos et al., 1999, J. Immunol. 162:5671–5675 and GenBank accession number HSA132337 (human CCR9)

Bonini et al., 1997, DNA Cell Biol. 16:1249–1256 and GenBank accession number HSU9488 (human CCR10)

PCR reactions can be carried out with a variety of thermostable enzymes including but not limited to Ampli- Taq, AmpliTaq Gold, or Vent polymerase. For AmpliTaq, reactions can be carried out in 10 mM Tris-Cl, pH 8.3, 2.0 mM $MgCl_2$, 200 µM of each dNTP, 50 mM KCl, 0.2 µM of each primer, 10 ng of DNA template, 0.05 units/µl of AmpliTaq. The reactions are heated at 95° C. for 3 minutes and then cycled 35 times using suitable cycling parameters, including, but not limited to, 95° C., 20 seconds, 62° C., 20 seconds, 72° C., 3 minutes. In addition to these conditions, a variety of suitable PCR protocols can be found in *PCR Primer, A Laboratory Manual*, edited by C. W. Dieffenbach and G. S. Dveksler, 1995, Cold Spring Harbor Laboratory Press; or *PCR Protocols: A Guide to Methods and Applications*, Michael et al., eds., 1990, Academic Press.

It is desirable to sequence the clones obtained by the herein-described methods, in order to verify that the desired chemokine receptor has in fact been obtained. The cDNA clones can be subcloned into suitable cloning vectors or expression vectors, e.g., the mammalian expression vector pcDNA3.1 (Invitrogen, San Diego, Calif.) or other expression vectors known in the art or described herein.

As an alternative to the above-described PCR methods, cDNA clones encoding chemokine receptors can be isolated from cDNA libraries using as a probe oligonucleotides specific for the desired chemokine receptor and methods well known in the art for screening cDNA libraries with oligonucleotide probes. Such methods are described in, e.g., Sambrook et al., 1989, *Molecular Cloning: A Laboratory Manual*; Cold Spring Harbor Laboratory, Cold Spring Harbor, N.Y.; Glover, D. M. (ed.), 1985, *DNA Cloning: A Practical Approach*, MRL Press, Ltd., Oxford, U.K., Vol. I, II. Oligonucleotides that are specific for particular chemokine receptors and that can be used to screen cDNA libraries can be readily designed based upon the known DNA sequence of the chemokine receptor and can be synthesized by methods well-known in the art.

In a similar manner, CD4 and viral proteins can be expressed recombinantly on the surfaces of the cells used in the present invention. Published sequences can be used to isolate and clone CD4 and viral proteins into suitable expression vectors via PCR or oligonucleotide hybridization, as for chemokine receptors. The sequence of a cDNA encoding human CD4 is disclosed in Maddon et al., 1985, Cell 42:93–104. The sequence of the Env gene from the HIV-1 strain BH8 is disclosed in Ratner et al., 1985, Nature 313:277–284. The sequence of the Env gene from the HIV-1 strain SF2 is disclosed in Sanchez-Pescador et al., 1985, Science 227:484–492. The sequence of the Env gene from the HIV-1 strain JR-FL is disclosed in O'Brien et al., 1990, Nature 348:69–73. The sequence of the Env gene from the HIV-1 strain SF162 is disclosed in Cheng-Mayer et al., 1990, J. Virol. 64:4390–4398. The construction of an expression vector that directs the expression of the Env protein from the HIV-1 strain JR-FL is described in International Patent Publication WO 96/41020 as well as the transfection of HeLa cells with the vector so as to express the Env protein in the HeLa cells.

In particular embodiments, the viral protein of the above-described methods is an HIV-1 Env protein. A large number of related HIV-1 Env proteins, from different strains of HIV-1, are known and are suitable for use in the present invention. In particular embodiments, the HIV-1 Env protein is an Env protein from a strain of HIV-1 selected from the group consisting of: the M-tropic strains JR-FL, JR-CSF, BaL, SF162, YU2; ADA; the T-tropic strains LAI, IIIB, MN, SF2, NL4-3, SF33, NDK and the dual tropic strains such as 89.6, 89.6P, DH123. Also, the viral protein may be from an HIV-2 strain (e.g., ROD, GUN, UC2, UC1, ST) or and SIV strain (e.g., SIVmac251, SIVagm, SIVmac239).

Env genes from virulent, primary field isolates of HIV are suitable for use in the present invention. This is accomplished by preparing cDNA copies of the Env genes from the viruses and then subcloning the genes into suitable expression vectors. Sequences for Env genes of many HIV strains are now publicly available on GENBANK and primary field isolates of HIV are available from the National Institute of Allergy and Infectious Diseases (NIAID) which has contracted with Quality Biological, Inc., 7581 Lindbergh Drive, Gaithersburg, Md. 20879, to make these viruses available. Such strains are also available from the World Health Organization (WHO) [Network for HIV Isolation and Characterization, Vaccine Development Unit, Office of Research, Global Program on AIDS, CH-1211 Geneva 27, Switzerland].

Alternatively, HIV Env genes can be cloned from infected PBMCs which have been activated by ConA treatment derived from patients with HIV. A preferred method for obtaining the viral genes is by PCR amplification from infected cellular genomes using specific oligomers flanking the desired Env gene. A second method for obtaining viral genes is by purification of viral RNA from the supernatants of infected cells and preparation of cDNA from this material with subsequent PCR.

Genomic DNA is purified from infected cell pellets by lysis in STE solution (10 mM NaCl, 10 mM EDTA, 10 mM Tris-HCl, pH 8.0) to which Proteinase K and SDS are added to 0.1 mg/ml and 0.5% final concentrations, respectively. This mixture is incubated overnight at 56° C. and extracted with 0.5 volumes of phenol:chloroform:isoamyl alcohol (25:24:1). The aqueous phase is then precipitated by addition of sodium acetate to 0.3 M final concentration and two volumes of cold ethanol. After pelleting the DNA from solution the DNA is resuspended in 0.1×TE solution (1×TE=10 mM Tris-HCl, pH 8.0, 1 mM EDTA). At this point SDS is added to 0.1% with 2 U of RNAse A with incubation for 30 minutes at 37° C. This solution is extracted with phenol/chloroform/isoamyl alcohol and then precipitated with ethanol as before. DNA is resuspended in 0.1×TE and quantitated by measuring its ultraviolet absorbance at 260 nm. Samples are stored at −20° C. until used for PCR.

PCR is performed using the Perkin-Elmer Cetus kit and procedure using the following sense and antisense oligomers for gp160: 5'-GA AAG AGC AGA AGA CAG TGG CAA TGA-3' (SEQ.ID.NO.:4), and 5'-GGG CTT TGC TAA ATG GGT GGC AAG TGG CCC GGG C ATG TGG-3' (SEQ.ID.NO.:5), respectively. These oligomers add an SrfI site at the 3'-terminus of the resulting DNA fragment. PCR-derived segments are cloned into suitable vectors.

In preferred embodiments of the present invention, cells are used that have been transfected with DNA encoding an HIV-1 Env protein so as to express the Env protein on the surface of the cells. HIV-1 Env consists of two noncovalently associated subunits generated by cleavage of the gp160 precursor. One subunit, gp120, is heavily glycosylated and found on the external side of the cell membrane. gp120 is derived from the N-terminal portion of the precursor and contains a binding site for CD4. The other subunit, gp41, spans the cell membrane and is derived from the C-terminal portion of the precursor. The amino terminal portion of gp41 contains a hydrophobic fusion peptide, which is involved in the fusion of the cellular and HIV-1 membranes. Env is found as a trimer on the surface of virions or infected cells. The trimer is held together by non-covalent interactions mediated by gp41. The extensive knowledge of the structure and biology of the HIV-1 Env protein allows for the use of many different versions of this protein, as discussed below.

In addition to the native, wild-type forms of HIV-1 Env proteins, chemokine receptors, and CD4, recombinantly produced mutated or variant forms of these proteins can be used in the methods of the present invention. Such mutants and variants would have amino acid sequences that differ somewhat from wild-type but would retain the ability to mediate membrane fusion. Such mutants and variants can be made by methods well known in the art. For example, see Ausubel et al., *Current Protocols in Molecular Biology*, Vol. 1, Ch. 8, 1989 and Supplements (John Wiley & Sons, Inc.); Oxender & Fox, eds., 1987, *Protein Engineering* (A. Liss, Inc.); Ehrlich ed., 1989, *PCR Technology* (Stockton Press).

One skilled in the art would produce such mutants and variants by changing only those amino acids that do not have an important role in mediating fusion. Such amino acids are those, e.g., in the Env protein that are important for CD4 or chemokine receptor binding. One skilled in the art would be guided in the production of such mutants and variants by the many studies that have determined the various regions of HIV-1 Env proteins and chemokine receptors that are important for mediating fusion. The residues of gp120 that are important for CD4 binding are disclosed in Lasky et al., 1987, Cell 50:975–985; Cordonnier et al., 1989, Nature 340:571–574; Cordonnier et al., 1989, J. Virol. 63:4464–4468; Olshevsky et al., 1990, J. Virol. 64:5701–5707; Kowalski et al., 1987, Science 237:1351–1355. Residues of gp120 that are important for chemokine receptor binding are disclosed in Feng et al., 1996, Science 272:872–877; Choe et al., 1996, Cell 85:1135–1148; Deng et al., 1996, Nature 381:661–666; Dragic et al., 1996, Nature 381:667–673; Doranz et al., 1996, Cell 85:1149–1158; Alkhatib et al., 1996, Science 272:1955–1958; Cocchi et al., 1996, Nature Med. 2:1244–1247; Bieniasz et al., 1997, EMBO J. 16:2599–2609; Speck et al., 1997, J. Virol. 71:7136–7139, where it is disclosed that the third variable loop (V3) is important for chemokine receptor binding.

The gp143 HIV-1 Env protein variant specifically exemplified herein is an example of a variant protein that can be used in the present invention.

Particularly preferred mutants and variants are those in which the amino acid sequence of the mutant or variant differs from the wild-type sequence by one or more conservative substitutions. A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutarnic acid for aspartic acid).

Under some circumstances, with certain strains of virus, fusion mediated by viral proteins and chemokine coreceptors has been observed to be independent of CD4. See, e.g., Endres et al., 1996, Cell. 87:745–756; Reeves et al., 1997, Virology 231:130–134; Potempa et al., 1997, J. Virol. 71:4419–4424; Reeves & Schulz, 1997, J. Virol. 71:1453–1465 for CD4independent fusion of HIV-2. See, Potempa et al., 1997, J. Virol. 71:4419–4424; Martin et al., 1997, Science 278:1470–1473; Edinger et al., 1997, Proc. Natl. Acad. Sci. USA 94:14742–14747 for CD4-independent fusion of SIV. See Bandres et al., 1998, J. Virol. 72:2500–2504; Hesselgesser et al., 1997, Curr. Biol. 7:112–121; Dumonceaux et al., 1998, J. Virol. 72:512–519 for CD4-independent fusion of HIV-1. Accordingly, when the methods of the present invention are practiced with certain viral proteins, these methods can be practiced without the use of a cell expressing CD4.

In addition to inhibitors of HIV-1, the present invention can be used to identify inhibitors of other viruses. For example, poxviruses are a family of viruses that infect cells by a process that includes fusion of infected cells with uninfected cells. Myxoma virus is a member of the poxvirus family that induces a lethal systemic disease in rabbits. Rodent fibroblasts, such as NIH 3T3 cells, cannot be infected by myxoma virus. However, if such rodent cells are transfected with DNA encoding human CD4 and human chemokine receptors such as CCR1, CCR5, or CXCR4, the cells are converted to cells that can be infected by myxoma virus (Lalani et al. 1999, Science 286:1968–1971). Thus, the present invention can be practiced in an embodiment where the first cell is a myxoma virus infected cell, or a cell that has been transfected with DNA encoding a myxoma virus protein that mediates cell fusion, where the first cell contains a fluorescent substrate of β-lactamase, and where the first cell is mixed with a second cell that contains a human chemokine receptor and also expresses β-lactamase. Fusion of the two cells is detected by measuring the ratio of FRET from the substrate of β-lactamase, as in other embodiments described herein.

The present invention can be used in an embodiment that identifies inhibitors of cellular protein interactions. For example, a cellular receptor can be expressed on a first cell, which first cell also expresses a viral fusion protein (e.g., simian virus 5 F protein). When the first cell is incubated with a second cell, which second cell expresses the appropriate cellular ligand for the cellular receptor, the interaction mediated by the cellular receptor and its ligand brings the first and second cells into close proximity. This allows the SV5 F protein to mediate membrane fusion of the first and second cells. If one of the first or second cells expresses β-lactamase and the other cell contains a fluorescent substrate of β-lactamase, fusion of the two cells can be detected by measuring the amount of FRET from the substrate of β-lactamase, as in other embodiments described herein. If this embodiment is carried out in the presence of a substance that is an inhibitor of the interaction between the cellular receptor and its ligand, the first and second cells will not be brought into close proximity, due to the presence of the inhibitor. Thus, the viral protein will not be able to mediate fusion. This lack of fusion due to the inhibitor can be detected by the measurement of FRET.

Accordingly, the present invention provides a method for identifying inhibitors of the interaction of a cellular receptor and its ligand comprising:

(a) providing a first cell that expresses a cellular receptor;

(b) providing a second cell that expresses a ligand of the cellular receptor;

where either:

(i) the first cell expresses β-lactamase and the second cell does not and the second cell contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer FRET) can occur when the linker is intact but does not occur when the linker has been cleaved; or (ii) the second cell expresses β-lactamase and the first cell does not and the first cell contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved;

and where either the first cell or the second cell expresses a viral protein that can mediate fusion of the first and the second cells only if the first and second cells are brought into close proximity by the interaction of the cellular receptor and its ligand;

(c) mixing the first and second cells in the presence and the absence of a substance such that the first and second cells will be brought into close proximity by the interaction of the cellular receptor and its ligand in the absence of the substance;

(d) measuring the amount of FRET in step (c) in the presence and in the absence of the substance;

where if the amount of FRET in the presence of the substance is greater than the amount of FRET in the absence of the substance, then the substance is an inhibitor of the interaction of the cellular receptor and its ligand.

In particular embodiments, the cellular receptor/ligand pair is selected from the group consisting of: Fas/FasL; T cell receptor/MHC I protein; T cell receptor/MHC II protein; GPIIb/IIIa receptor/fibrinogen; presenilin-1/APP; and presenilin-2/APP.

The fluorescent substrate used in the assays for transcriptional activation described by Zlokarnik et al., 1998, Science 279:84–88 is known as CCF2/AM. CCF2/AM is used in a preferred embodiment of the present invention. The structure of CCF2/AM is CCF2 contains 7-hydoxycoumarin as the FRET donor at the 7 position of the cephalosporin moiety. The 7-hydroxycoumarin has a 6-chloro substituent to lower the pKa of CCF2 to 5.1, thus making fluorescence independent of pH at pH values above 6, as well as a glycine spacer between the coumarin and the cephalosporin moiety. The fluorescent acceptor is fluorescein, which is attached to the 7' position of the cephalosporin moiety via a thioether linkage.

Figure 2:
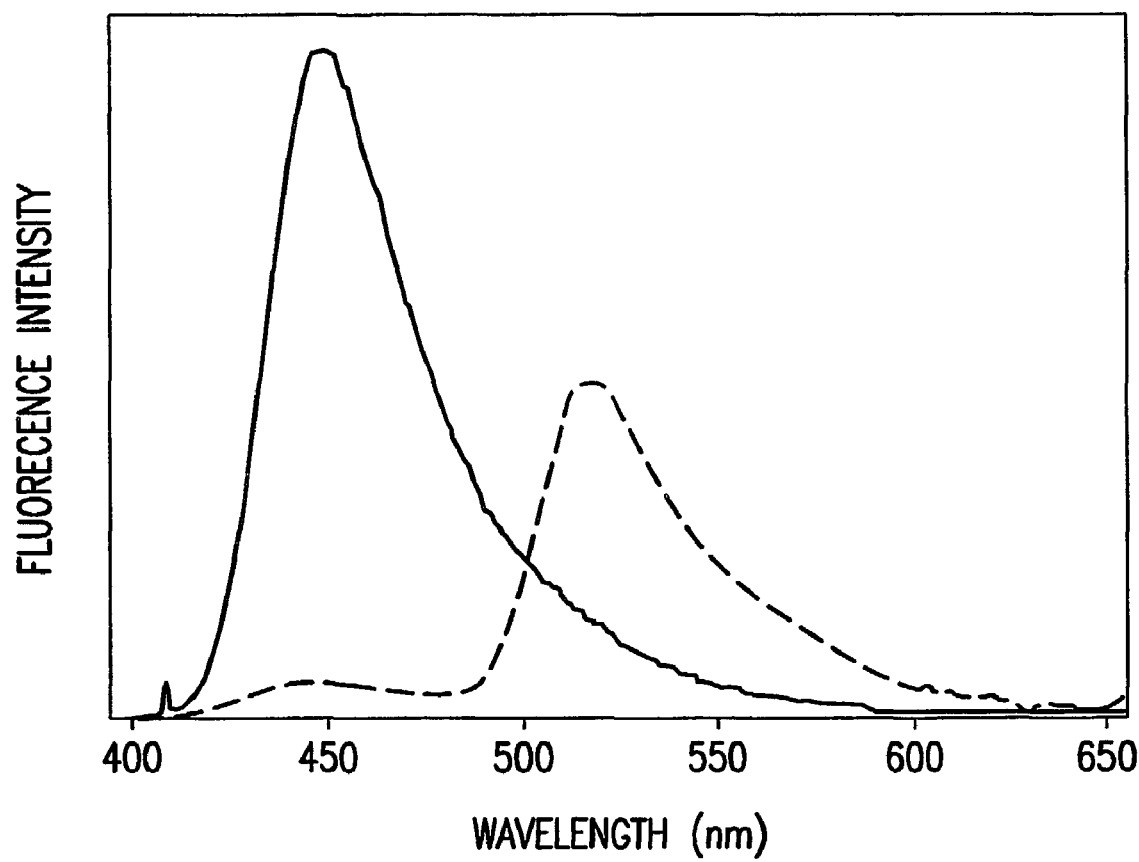
FIG. 2 illustrates the emission spectrum of intact CCF2 (dashed line) and CCF2 after the fluorescein has been cleaved away by β-lactamase (solid line).

Excitation of the coumarin donor of intact CCF2 at 409 nm gives rise to FRET emission from the fluorescein acceptor having a peak at 520 nm. After cleavage of CCF2, and the separation of the coumarin and fluorescein, excitation of the coumarin donor gives rise to fluorescent emission from the coumarin having a peak at 447 nm. FIG. 2 illustrates the emission spectrum of intact CCF2 and CCF2 after the fluorescein has been cleaved away by β-lactamase activity. Of course, excitation need not be done at and emission need not be measured at precisely the wavelengths mentioned above. For example, one could excite at 395 nm and measure emission at 530 nm and 460 nm.

Generally, the ratio of donor emission to acceptor emission is determined as a way of measuring the amount of FRET. A low ratio indicates an intact CCF2 structure and

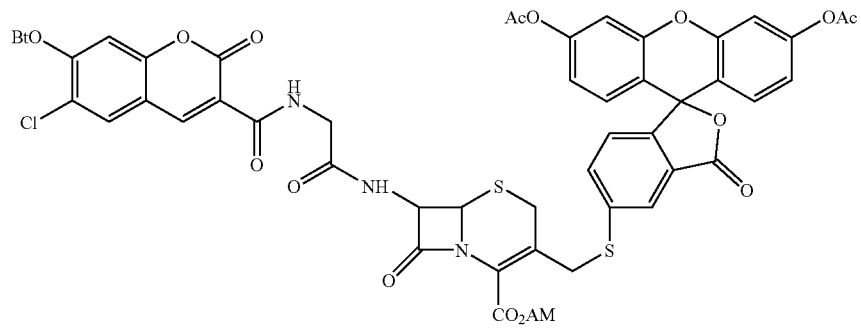

where Ac=acetyl; Bt=butyryl; and AM=acetoxymethyl.

CCF2/AM contains several ester functionalities. These esters make CCF2/AM membrane-permeant. Because of this membrane-permeant property, CCF2/AM will be taken up by cells growing in tissue culture following addition to the media. After uptake, intracellular esterases cleave the esters, giving rise to CCF2, which is trapped intracellularly due to its many negative charges. The structure of CCF2 is thus little fusion; a high ratio indicates that CCF2 has been cleaved by β-lactamase and thus relatively more fusion. Accordingly, in a preferred embodiment, the present invention is practiced by using emission ratioing to measure FRET. In principle, one could measure FRET by monitoring either (a) a decrease in the emission of the donor fluorescent reagent following stimulation at the donor's absorption wavelength and/or (b) an increase in the emission of the

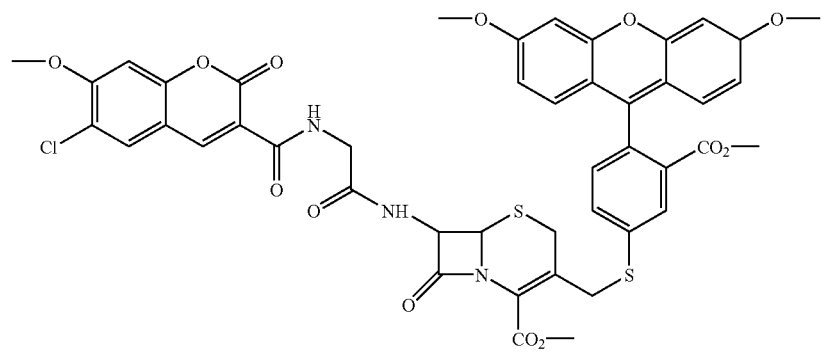

acceptor reagent following stimulation at the donor's absorption wavelength. In practice, FRET is most effectively measured by emission ratioing. Emission ratioing refers to measuring the change in the ratio of emission by the acceptor over emission by the donor. An increase in this ratio signifies that energy is being transferred from donor to acceptor and thus that FRET is occurring. Emission ratioing can be measured by employing a laser-scanning confocal microscope. Emission ratioing is preferably done by splitting the emitted light from a sample with a dichroic mirror and measuring two wavelength bands (corresponding to the donor and the acceptor emission wavelengths) simultaneously with two detectors. Alternatively, the emitted light can be sampled consecutively at each wavelength (by using appropriate filters) with a single detector. In any case, these and other methods of measuring FRET are well known in the art.

The use of emission ratioing in the present methods eliminates many variables that confounded accurate quantitation in previous methods such as cell size, cell number, probe concentration, and light intensity. The methods of the present invention are easily monitored with a fluorescence microscope or a plate reader. In addition, the readout does not depend on gene transcription, thus avoiding a bias for selecting transcriptional inhibitors. Since readout is immediate, cell lysis is not required as in most transcription based assays. The present invention can be readily adapted for use in 96 well microtiter plates or even in higher density well plates, allowing for its use in high throughput screening programs.

The present invention provides a method for determining the amount of fusion that occurs between two cells via the measurement of fluorescence resonance energy transfer (FRET) comprising:

(a) providing a first cell that expresses β-lactamase;

(b) providing a second cell that does not express β-lactamase but contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where FRET can occur when the linker is intact but does not occur when the linker has been cleaved;

(c) measuring the donor/acceptor emission ratio from the substrate in the second cell in the absence of fusion between the first and second cells;

(d) bringing the first and second cells into contact under conditions such that fusion occurs;

(e) measuring the donor/acceptor emission ratio from the substrate after fusion has occurred;

where the ratio of the donor/acceptor emission ratio measured in step (e) over the donor/acceptor emission ratio measured in step (c) represents the amount of fusion that has occurred, with larger ratios indicating greater amounts of fusion.

The present invention also provides a method of identifying an inhibitor of the fusion of a first and a second cell comprising:

(a) providing a first cell that expresses β-lactamase where the first cell is a suspension cell;

(b) providing a second cell that does not express β-lactamase where the second cell is an adherent cell;

(c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance;

(d) washing away any unfused first cells;

(e) exposing the fused cells to a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved under conditions and for a sufficient time such that the substrate is taken up into the cytoplasm of the fused cells and into the cytoplasm of any unfused adherent cells;

(f) measuring the donor/acceptor emission ratio from the substrate in the fused cells;

where if the donor/acceptor emission ratio is smaller in the presence of the substance than in the absence of the substance, then the substance is an inhibitor of the fusion of the first and the second cells.

CCF2 is meant to be illustrative of certain preferred embodiments of the invention. The invention can also be practiced with other fluorescent substrates.

A general formula for fluorescent substrates of β-lactamase that are suitable for use in the present invention is:

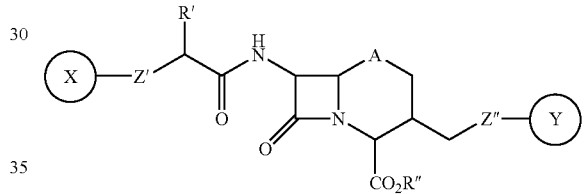

where:

one of X and Y is a fluorescent donor moiety or an ester derivative of said fluorescent donor moiety, and the other is a fluorescent acceptor or an ester derivative of said fluorescent acceptor moiety; where fluorescence resonance energy transfer can occur between said fluorescent donor moiety and said fluorescent acceptor moiety;

R' is selected from the group consisting of H, lower alkyl and $(CH_2)_nOH$, in which n is 0 or an integer from 1 to 5;

R" is selected from the group consisting of H, physiologically acceptable metal and ammonium cations, $-CHR^2OCO(CH_2)_nCH_3$, $-CHR^2OCOC(CH_3)_3$, -acylthiomethyl, -acyloxy-alpha-benzyl, -delta-butyrolactonyl, -methoxycarbonyloxymethyl, -phenyl, -methylsulphinylmethyl, -beta-morpholinoethyl, -dialkylaminoethyl, -acyloxyalkyl, -dialkylaminocarbonyloxymethyl and -alkyl, in which $R^2$ is selected from the group consisting of H and lower alkyl and in which n is 0 or an integer from 1 to 5; A is selected from the group consisting of S, O, SO, $SO_2$ and $CH_2$; and Z' and Z" are linkers for the fluorescent donor and acceptor moieties.

Preferably, Z' is selected from the group consisting of a direct bond $-(CH_2)_nCONR^2(CH_2)_m-$, $-(CH_2)_nNR^2CO(CH_2)_m-$, $-(CH_2)_nNR^2CONR^2(CH_2)_m-$, $-(CH_2)_nNR^3CSNR^2(CH_2)_m-$, $-(CH_2)_nCONR^3(CH_2)_pCONR^2(CH_2)_m-$, $-(CH_2)_n-$, $-(CH_2)_nNR^3CO(CH_2)_pS(CH_2)_m-$, $-(CH_2)_nS(CH_2)_m-$, $-(CH_2)_nO(CH^2)_m-$, $-(CH_2)_nNR^2(CH_2)_m-$, $-(CH_2)_nSO_2NR^2(CH_2)_m-$, $-(CH_2)_nCO_2(CH_2)_m-$,

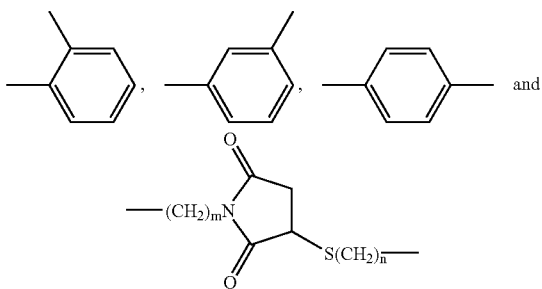

in which $R^2$ is selected from the group consisting of H and lower alkyl; $R^3$ is selected from the group consisting of hydrogen and lower alkyl; and each of n, m and p is independently selected from the group consisting of 0 and integers from 1 to 4.

Preferably, Z" is selected from the group consisting of a direct bond to a heteroatom in Y, —O(CH$_2$)$_n$—, —S(CH$_2$)$_n$—, —NR$^2$(CH$_2$)$_n$—, —N$^+$R$^2$$_2$(CH$_2$)$_n$—, —OCONR$^2$(CH$_2$)$_n$—, —O$_2$C(CH$_2$)$_n$—, —SCSNR$^2$(CH$_2$)$_n$—, —SCSO(CH$_2$)$_n$—, and

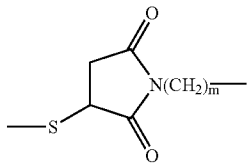

in which $R^2$ is selected from the group consisting of H and lower alkyl; and each of n and m is independently selected from the group consisting of 0 and integers from 1 to 4.

Suitable fluorescent moieties for the β-lactamase substrates described herein, as well as methods of making the β-lactamase substrates disclosed herein, are disclosed in U.S. Pat. No. 5,741,657, the disclosures of which are incorporated by reference herein.

The linker in the fluorescent substrate that is cleaved by β-lactamase is preferably a cephalosporin. This is because any molecule (such as a fluorescent moiety) that can be chemically attached to the 3' substituent of a cephalosporin is released upon cleavage of the β-lactam ring of the cephalosporin by β-lactamase (Albrecht et al., 1991, J. Med. Chem. 34:669–675). Thus, a fluorescent moiety attached to the 3' substituent will be released upon cleavage and will diffuse away from another fluorescent moiety that remains attached to the rest of the substrate.

A variety of β-lactamases are known in the art and are suitable for use in the present methods. One particularly well-studied form of β-lactamase is the product of the Amp$^r$ gene of *E. coli*, TEM-1 β-lactamase (Sutcliffe, 1978, Proc. Natl. Acad. Sci. USA 75:3737–3741). A version of TEM-1, with its signal sequence deleted so that it accumulates in the cytoplasm, is disclosed in Kadonaga et al., 1984, J. Biol. Chem. 259:2149–2154.

β-lactamases are produced by a variety of bacteria and many β-lactamases are have been well studied. For example, *Staphlyococcus aureus* produces PC1 β-lactamase; *Bacillus cereus* produces a β-lactamase known as β-lactamase I; and *Escherichia coli* produces RTEM β-lactamase (Christensen et al., 1990, Biochem J. 266:853–861). All that is necessary for a particular β-lactamase to be suitable for use in the present invention is that it be capable of cleaving the fluorescent substrate in such a way that the two fluorescent moieties of the substrate can diffuse away from each other following cleavage. This can be easily tested and thus the suitability of a particular β-lactamase can be easily determined.

The amino acid sequences of a variety of suitable β-lactamases are disclosed in Ambler, 1980, Phil. Trans. R. Soc. Lond. (Ser. B.) 289:321–331. One of skill in the art can readily synthesize synthetic DNA sequences that encode these β-lactamases. Alternatively, these β-lactamases can be cloned from natural sources. DNA sequences encoding β-lactamases can be placed into suitable expression vectors and transfected into cells for use in the methods of the present invention. A DNA sequence encoding a particular β-lactamase that can be used in the methods of the present invention is shown in SEQ.ID.NO.:1 of U.S. Pat. No. 5,741,657 while the corresponding amino acid sequence is shown as SEQ.ID.NO.:2 of U.S. Pat. No. 5,741,657. A plasmid containing this DNA (pTG2del1) is described in Kadonaga et al., 1984, J. Biol. Chem. 259:2149–2154.

Moore et al., 1997, Anal. Biochem. 247:203–209 describes a method for engineering a form of RTEM1 β-lactamase that is maintained intracellularly by eukaryotic cells. DNA encoding the native signal sequence of RTEM1 β-lactamase is removed and replaced with a methionine codon. Sequences that provide for optimal translational efficiency in eukaryotes are placed immediately upstream of this methionine by PCR. This modified β-lactamase coding sequence is then cloned into expression vector pRc-CMV (Invitrogen, San Diego, Calif.). This places the coding sequences under the control of the human intermediate early cytomegalovirus promoter and provides a bovine growth hormone polyadenylation sequence. This construct, known as pCMV-BL, was able to direct the expression of active β-lactamase in the cytoplasm of mammalian cells.

A variety of expression vectors can be used to recombinantly express DNA encoding β-lactamases, HIV-1 Env proteins, chemokine receptors, and CD4 for use in the present invention. Commercially available expression vectors which are suitable include, but are not limited to, pMC1neo (Stratagene), pSG5 (Stratagene), pcDNAI and pcDNAIamp, pcDNA3, pcDNA3.1, pCR3.1 (Invitrogen, San Diego, Calif.), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), pCl.neo (Promega), pTRE (Clontech, Palo Alto, Calif.), pV1Jneo, pIRESneo (Clontech, Palo Alto, Calif.), pCEP4 (Invitrogen, San Diego, Calif.), pSC11, and pSV2-dhfr (ATCC 37146). The choice of vector will depend upon cell type in which it is desired to express the β-lactamase, HIV-1 Env protein, chemokine receptor, and CD4, as well as on the level of expression desired, and the like.

The expression vectors can be used to transiently express or stably transfer the genes. The transient expression or stable transfer of genes into cells is well known in the art. See, e.g., Ausubel et al., 1995, "Introduction of DNA into mammalian cells," in *Current Protocols in Molecular Biology*, sections 9.5.1–9.5.6 (John Wiley & Sons, Inc.).

The fluorescent substrates of β-lactamase that are used in the present invention are generally used at a final concentration of from about 50 nM to about 50 µM, preferably from about 100 nM to about 10 µM, more preferably from about 500 nM to about 5 µM, and most preferably at a concentration of about 1 µM in the media or buffer in which the cells to be fused are present. Generally, this concentration can be adjusted so that the intracellular concentration of the substrate, after loading into the cells, is about 50 to 100 μM.

The present invention can be carried out with cells that are present in conventional tissue culture media and/or buffers, e.g., Iscove's Modified Dulbecco's Medium, RPMI 1640 (with or without 10 mM HEPES), Hank's Balanced Salt Solution, Dulbecco's Modified Eagle's Medium, Phosphate buffered saline (PBS). If the substrate in its intracellular form is polyanionic, an inhibitor of non-specific anion transport, such as probenecid, at about 2.5 mM, can be added in order to promote retention of the substrate within the cells.

Conditions suitable for fusion to occur can be readily determined by one skilled in the art, guided by the many publications in which fusion of cells mediated by viruses has been reported. In particular, the scientific literature is rich in reports of the study of HIV-1 Env mediated fusion. Such reports can guide the skilled person in selecting suitable conditions for the practice of the present invention.

The methods of the present invention are suitable for high throughput screening. Accordingly, it may be advantageous to carry out the methods in multi-well microtiter plates. Examples of such plates are: Costar Special Optics plates; Costar black clear bottom plates (catalog numbers 3603 or 3904).

Many different cells can be used in the present invention. It is not necessary that the two types of cells that are used in the present invention be completely different. It is enough that the two types of cells express different proteins that mediate fusion. For example, one could begin with a single line of cells and, by transfecting an HIV-1 Env protein and β-lactamase into a first portion of the cells and transfecting CD4 and a chemokine receptor into a second portion of the cells, one would then have the requisite two types of cells. Of course, the invention may be practiced with two types of cells that are completely distinct. Such is the case for the embodiment described herein that uses Chinese hamster ovary (CHO) cells and Jurkat cells. Cells, such as Jurkat cells, that naturally express proteins that are capable of mediating fusion, can be used. One could also used human primary lymphocytes which have been transfected with β-latamase to fuse with envelope expressing cells. This extends the utility of the method to include studies of in vivo derived cells (i.e., the invention is not limited to the use of cell lines).

Cells that may be used include, but are not limited to, mammalian cells such as cell lines of human, bovine, porcine, monkey and rodent origin. Cell lines derived from mammalian species which are suitable are commercially available and include, but are not limited to, L cells L-M (TK$^{31}$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), Chinese hamster ovary (CHO) cells, including CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), CPAE (ATCC CCL 209), Saos-2 (ATCC HTB-85), ARPE-19 human retinal pigment epithelium (ATCC CRL-2302), Jurkat cells, GH3 cells, and baby hamster kidney (BHK) cells. Particularly preferred cells are T cells. Particularly preferred T cells are Jurkat cells (ATTC TIB-152) and the modified Jurkat T cell line JK.CMV-blaM.S1. C1 (Aurora Biosciences, San Diego, Calif.).

Jurkat cells naturally express CD4 and CXCR4 and thus are particularly suitable for use in the present invention. Also particularly suitable are 293T cells. 293T cells are commonly used for high levels of transient expression since they express SV40 large T antigen. An example of their use can be found in Pear et al., 1993, Proc. Natl. Acad. Sci. USA 90:8392–8396.

Other cells that may be used in the present invention include: a HeLa cell line which stably expresses the Env protein from the M-tropic JR-FL strain of HIV-1 described in Koyanagi et al., 1987, Science 236:819–822; the PM1 T lymphoblastoid cell line described in Lusso et al., 1995, J. Virol. 69:3712–3720.

In preferred embodiments, the cells are human cells. When the invention is practiced using non-human cells, it is generally preferable to transfect the non-human cells so that they express human CD4 and a human chemokine receptor rather than relying on the endogenous CD4 and chemokine receptors. Insect cell lines such as the Drosophila Schneider S2 cells (ATTC CRL-1963), SF9, (ATCC CRL-1711) and SF21 (Invitrogen, San Diego, Calif.) are also suitable.

The present invention provides several advantages over prior art methods:
- the present invention does not rely upon the activation of gene transcription to monitor fusion
- the readout from β-lactamase activity in the fused cells is very fast and can be recorded in as little time as 1 hour (routinely about 2–3 hours)
- the determination of β-lactamase activity is sensitive and readily quantitated
- it is not necessary to use two different fluorescent dyes; only a single fluorescent dye is used.

Furthermore, the use of the engineered HIV envelope construct gp143 in a preferred embodiment in order to generate stable cell lines provides high levels of expression for the envelope protein and increases both the robustness and reproducibility of the assay.

The assay described in International Patent Publication WO 96/41020 requires the use of two different dyes, each of which must be capable of being integrated into the cell membranes of two cell types. The success of the assay depends on the two dyes becoming juxtaposed within the same lipid membrane at a suitably short distance from each other such that FRET can occur between the dyes. In contrast, the present invention requires only a single dye, where the single dye is present primarily in the cytoplasm of cells.

The present invention includes pharmaceutical compositions comprising inhibitors of viral (e.g., HIV-1) infection that have been identified by the above-described methods. The inhibitors are generally combined with pharmaceutically acceptable carriers to form pharmaceutical compositions. Examples of such carriers and methods of formulation of pharmaceutical compositions containing inhibitors and carriers can be found in Remington's Pharmaceutical Sciences. To form a pharmaceutically acceptable composition suitable for effective administration, such compositions will contain a therapeutically effective amount of the inhibitors.

Therapeutic or prophylactic compositions are administered to an individual in amounts sufficient to treat or prevent viral infection. The effective amount can vary according to a variety of factors such as the individual's condition, weight, gender, and age. Other factors include the mode of administration. The appropriate amount can be determined by a skilled physician.

Compositions can be used alone at appropriate dosages. Alternatively, co-administration or sequential administration of other agents can be desirable.

The compositions can be administered in a wide variety of therapeutic dosage forms in conventional vehicles for administration. For example, the compositions can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts.

Advantageously, compositions can be administered in a single daily dose, or the total daily dosage can be administered in divided doses of two, three, four, or more times daily. Furthermore, compositions can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compositions is selected in accordance with a variety of factors including type, species, age, weight, sex and medical condition of the patient; the severity of the condition to be treated; the route of administration; the renal, hepatic and cardiovascular function of the patient; and the particular composition thereof employed. A physician of ordinary skill can readily determine and prescribe the effective amount of the composition required to prevent, counter or arrest the progress of the condition. Optimal precision in achieving concentrations of composition within the range that yields efficacy without toxicity requires a regimen based on the kinetics of the composition's availability to target sites. This involves a consideration of the distribution, equilibrium, and elimination of a composition.

The following non-limiting examples are presented to better illustrate the invention.

EXAMPLE 1

A CHO Cell/Jurkat Cell Embodiment of the Present Invention

A particular embodiment of the invention makes use of Chinese hamster ovary (CHO) cells (an adherent cell line) that have been transfected so as to express an HIV Env protein and Jurkat T cells (a suspension cell line) that have been transfected so as to express β-lactamase. In a particular version of this embodiment, a CHO cell line expressing a truncated version of a T-tropic Env (gp143/HXB2) was plated in 96-well, black, clear bottom microtiter plates and incubated overnight at 37° C. to allow the cells to attach. Jurkat cells expressing β-lactamase (and which naturally express CXCR4 and CD4) were added to the CHO cells and incubated at 37° C. for a period sufficient to allow fusion to occur. The non-fused cells were removed by washing and the fluorogenic 1β-lactamase substrate CCF2/AM was added to the remaining cells. After a 1 hour incubation at room temperature, cell fusion was measured by fluorescence on a fluorescence plate reader. The ratio of emission of the donor dye (7-hydroxycoumarin) over emission of the acceptor dye (fluorescein) was measured.

CCF2/AM is an esterified form of CCF2 that is membrane permeant. Once inside a cell, intracellular esterases hydrolyze the ester functionalities of CCF2/AM, releasing the polyanionic CCF2, which, due to its high level of negative charge, remains trapped in the cell. CCF2 contains two fluorophores, 7-hydroxycoumarin and fluorescein, attached to the a cephalosporin β lactam ring. In the intact substrate, excitation of the coumarin moiety at 395 nm results in fluorescence resonance energy transfer (FRET) to the fluorescein moiety, causing the fluorescein to emit a green fluorescence at 530 nm. If CCF2 is cleaved by β-lactamase, FRET is disrupted. In that case, excitation of the coumarin results in emission at 460 nm, giving rise to blue fluorescence. Blue fluorescence indicates the formation of fused cells, or syncytia, due to the pooling of cytoplasms of the Jurkat cells and the CHO cells, which results in the exposure of the β-lactamase substrate CCF2 from the CHO cells to the β-lactamase from the Jurkat cells. The persistence of green fluorescence indicates that CHO cells have not fused, and the CCF2 in the CHO cell cytoplasm has not been exposed to β-lactamase. Fusion is measured by observing the ratio of blue emission (460 nm) to green emission (530 nm). A high ratio indicates more fusion; a low ratio indicates less fusion.

A detailed protocol for this CHO cell/Jurkat cell embodiment of the present invention is as follows:

1. CHO cells expressing gp143/HXB2 were plated in 96-well black, clear-bottom plates (Costar catalogue number 3603) at $5 \times 10^4$ cells per well in 200 μl of medium per well. The medium was Iscove's Modified Dulbecco's Medium (Gibco catalogue number 12440-046) supplemented with: 10% fetal bovine serum, G418 (1 mg/ml), 1 mg/ml penicillin/streptomycin (Gibco catalogue number 15140-122), glutamine (2 mM), and HT (ATCC 71-X).

2. The cells were incubated overnight at 37° C.

3. The cells were washed 1× with 100 μl per well of serum-free Iscove's Modified Dulbecco's Medium (Gibco catalogue number 12440-046).

4. Jurkat T cells expressing β-lactamase were diluted to $1.6 \times 10^6$ cells/ml in serum-free medium (Iscove's Modified Dulbecco's Medium (Gibco catalogue number 12440-046) and 100 μl of this dilution (80,000 cells) was added to each well containing the CHO cells.

5. The CHO cells and Jurkat cells were incubated for 2 hours at 37° C.

6. The CHO cells and Jurkat cells were washed 2× with 100 μl per well of serum-free medium (Iscove's Modified Dulbecco's Medium (Gibco catalogue number 12440-046).

7. 100 μl of serum-free medium was added to each well (Iscove's Modified Dulbecco's Medium (Gibco catalogue number 12440-046).

8. 20 μl of 6× concentrated CCF2/AM (12 μM) in 11% ESS buffer was added to each well.

9. The fused cells loaded with CCF2/AM were incubated for 1 hour at room temperature with gentle rocking.

10. The plates were read on a Cytofluor II fluorescence plate reader (PerSeptive Biosystems) at 2 scans/cycle. One scan was done with excitation at 395 nm or 405 nm and emission at 460 nm and the other scan was done with excitation at 395 nm or 405 nm and emission at 530 nm.

Figure 3:
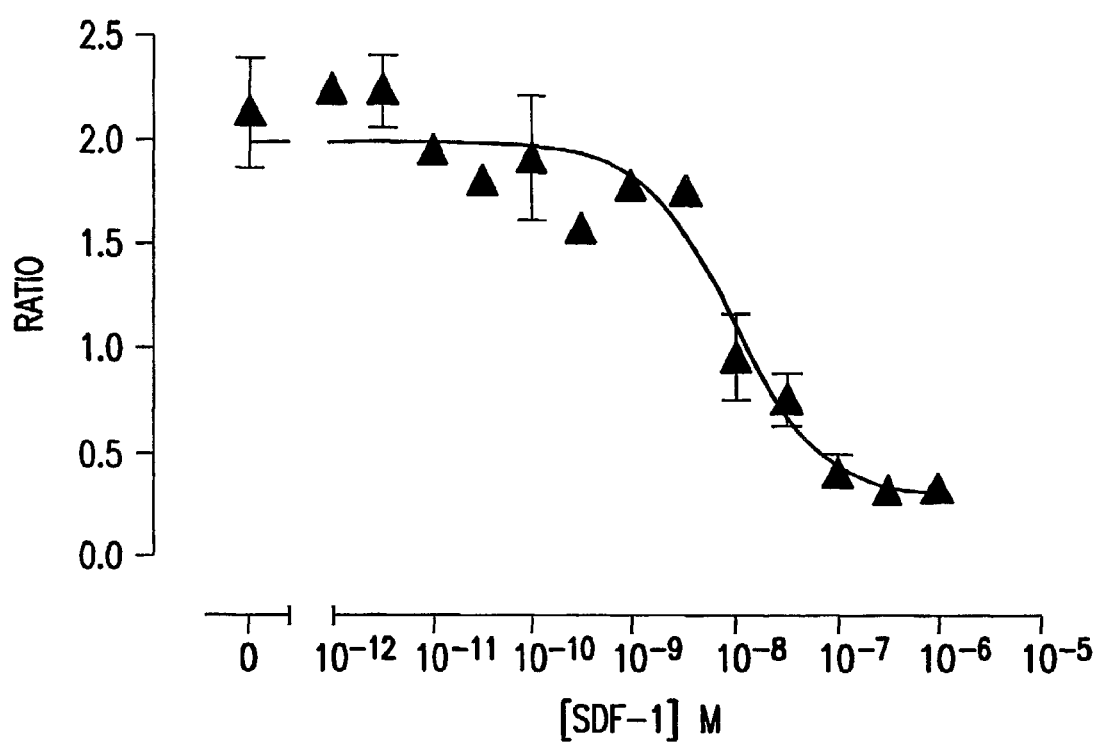
FIG. 3 is a graph showing dose-dependent inhibition of fusion mediated by CD4, CXCR4, and the HIV-1 Env protein gp143 by the natural ligand of CXCR4, SDF-1.
Figure 4:
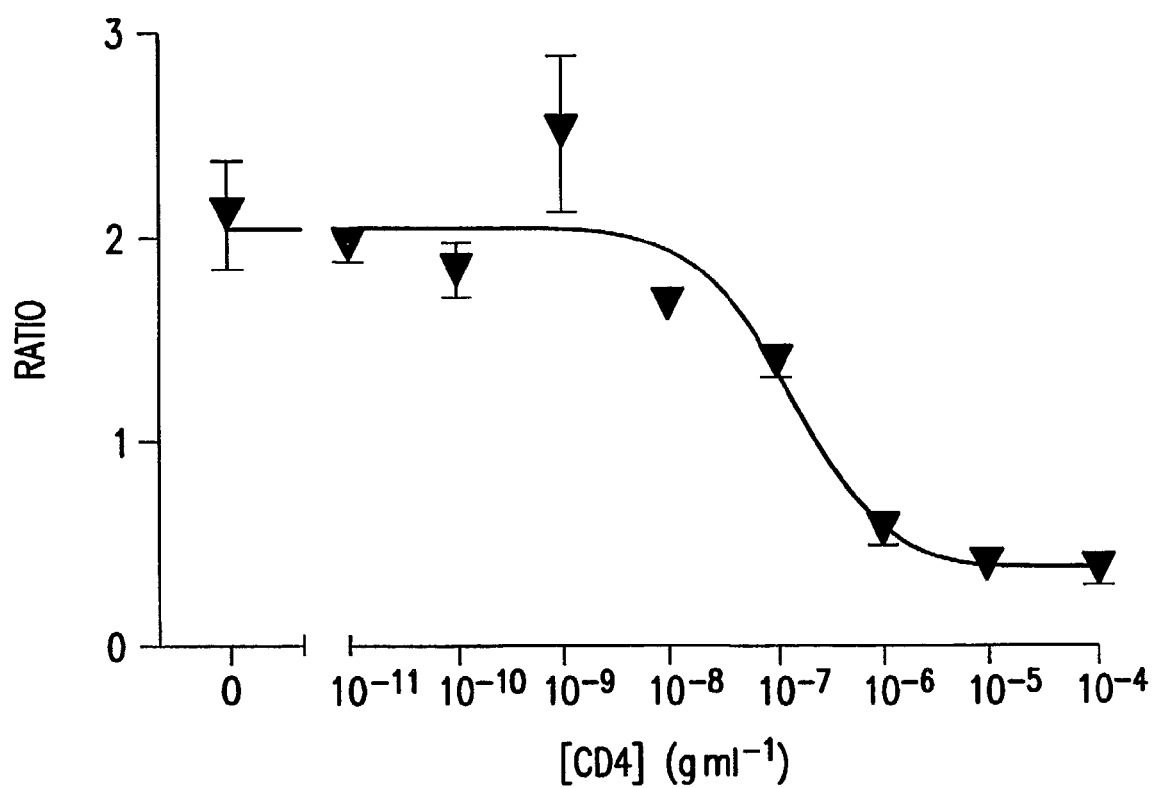
FIG. 4 is a graph showing dose-dependent inhibition of fusion mediated by CD4, CXCR4, and the HIV-1 Env protein gp143 by soluble CD4.

The above described CHO cell/Jurkat cell embodiment of the present invention has been validated by showing that fusion is inhibited by SDF-1 □PeproTech Inc., Rocky Hill, N.J.), the natural ligand for CXCR4, in a dose dependent fashion with an $IC_{50}$ of 13.4±2.6 nM (FIG. 3). Fusion is also inhibited by soluble CD4 (NEN Life Science Products, Inc., Boston, Mass.) with an $IC_{50}$ of 3.3 nM (FIG. 4) as well as by a monoclonal antibody (recombinant Mab designated IgG1 b12 produced from recombinant CHO cells) against the HIV envelope glycoprotein.

EXAMPLE 2

A 293T Cell/Jurkat Cell Embodiment of the Present Invention

The assay was carried out in 6-well polyD-lysine microtiter plates. 293T cells ($0.7 \times 10^6$ cells per well; about 70% confluent) were transiently transfected with 2 µg pVIJneo/gp143HXB2 per well using a Gibco/BRL LIPOFECTAMINE PLUS® kit and 24 hours later were overlayed for 1 hour at 37° C. with $2 \times 10^6$ Jurkat cells per well that constitutively express β-lactamase. Non-attached Jurkat cells were washed 3–4 times with tissue culture media and the 293T cells and remaining Jurkat cells were allowed to fuse for 3–4 hours at 37° C. The cells were then loaded with CCF2/AM (2 µM per well, final concentration). As a control, this experiment was repeated with 293T cells that were mock transfected and thus did not express gp143. Results were visualized by fluorescence microscopy and documented by photography. This showed that the mock transfected control cells fluoresced green, indicating intact CCF2 and thus lack of fusion. In contrast, the 293T cells that had been transfected with pVIJneo/gp143HXB2 and therefore expressed gp143 fluoresced blue and showed syncytia formation. This indicated that CCF2 had been cleaved by β-lactamase from the Jurkat cells which had fused with the 293T cells.

The 293T cells were maintained in DMEM, high glucose medium (GibcoBRL catalogue number 12430-047) supplemented with 10% heat-inactivated fetal bovine serum (GibcoBRL catalogue number 10438-026), 2 mM glutamine (GibcoBRL catalogue number 25030-081), 0.1 mM non-essential amino acids (GibcoBRL catalogue number 11140-050) and 1 mg/ml penicillin/streptomycin (GibcoBRL catalogue number 15140-122).

The Jurkat □-lactamase cells were maintained in RPMI 1640 with 25 mM HEPES (GibcoBRL catalogue number 22400-071), 10% heat-inactivated fetal bovine serum (GibcoBRL catalogue number 10438-026), 2 mM glutamine (GibcoBRL catalogue number 25030-081), 0.1 mM non-essential amino acids (GibcoBRL catalogue number 11140-050), 1 mM sodium pyruvate (GibcoBRL catalogue number 11360-070), 55 µM 2-mercaptoethanol (GibcoBRL catalogue number 21985-023) and 800 ug/ml G418 (GibcoBRL catalogue number 10131-027).

The assay described above was also practiced in 96-well format. 293 T cells (30,000 cells/well) were seeded in Costar Special Optics plates (catalogue number 3614) twenty four hours prior to transfection. Cells were transfected with 0.2 µg DNA utilizing LIPOFECTAMINE PLUS® (Gibco) following the manufacturer's protocol. Twenty four hours later, cells were washed twice with 100 µl of medium (DMEM supplemented with 10% heat-inactivated fetal bovine serum) and overlayed with 80,000 Jurkat cells (in this same medium) for 1 hour at 37° C. Non-attached Jurkat cells were washed off (rinsing three times with 100 µl medium), 100 µl medium was added, and cells allowed to fuse additional 4 hours at 37° C. To visualize and measure fusion, cells were then loaded with the □-lactamase substrate, CCF2/AM. Existing medium was replaced with 100 µl/well of serum-free medium (Iscove's Modified Dulbecco's Medium with 25 mM HEPES). 20 µl of 6× loading buffer was added to achieve a final concentration of 2 PM CCF2/AM, and 2.5 mM probenecid The cells were incubated for 1 hour at room temperature with gentle rocking. Results were documented by fluorescence microscopy utilizing a Zeiss Axiovert 100 Microscope (Carl Zeiss, Inc.) equipped with a 100 W mercury lamp and fitted with a long pass Dichroic mirror (425 nm-steep onset) utilizing a 405±10 nm Excitation filter and a 435 nm long-pass Emission filter. Mock transfected 293T cells failed to fuse with Jurkat cells, and thus lacked β-lactamase and fluoresced green. HXB2 Env-expressing cells fused with Jurkat cells and were visualized by the appearance of blue syncytia as a result of β-lactamase expression. Fusion was quantitated on the CytoFluor 4000 fluorescence plate reader (PerSeptive Biosystems) with all measurements recorded from the bottom of the wells. Fluorescence in the blue channel was measured after excitation at 395/20 nm by recording the emission at 460/40 nm. Fluorescence in the green channel was measured following excitation at 395/20 nm by recording the emission at 530/25 nm. Background for both channels was obtained by recording similar emission data from wells containing the same medium and CCF2 but lacking cells and was subtracted for both channels. The fusion ratio was generated by dividing the 460 emission (blue channel) values by the 530 emission (green channel) values. Typical results showed a 2.6 fold window with a fusion ratio of 1.54±0.003 for cells expressing gp143/HXB2 versus 0.58±0.03 for mock transfected cells.

EXAMPLE 3

Construction of the Env Expression Vector pVIJneo/gp143HXB2

The expression vector pV1J is described in International Patent Publication WO 94/21797. pV1Jneo was derived from pV1J by removing the ampicillin gene ($amp^r$) from pV1J and replacing it with the neomycin resistance gene. The $amp^r$ gene from the pUC backbone of pV1J was removed by digestion with SspI and Eam 1105I restriction enzymes. The remaining plasmid was purified by agarose gel electrophoresis, blunt-ended with T4 DNA polymerase, and then treated with calf intestinal alkaline phosphatase. The commercially available $kan^r$ gene, derived from transposon 903 and contained within the pUC4K plasmid (Pharmacia), was excised using the PstI restriction enzyme, purified by agarose gel electrophoresis, and blunt-ended with T4 DNA polymerase. This fragment was ligated with the pV1J backbone and plasmids with the $kan^r$ gene in either orientation were derived which were designated as pV1Jneo #'s 1 and 3. Each of these plasmids was confirmed by restriction enzyme digestion analysis, DNA sequencing of the junction regions, and was shown to produce similar quantities of plasmid as pV1J. Expression of heterologous gene products was also comparable to pV1J for these pV1Jneo vectors. We arbitrarily selected pV1Jneo#3, referred to as pV1Jneo herein, which contains the $kan^r$ gene in the same orientation as the $amp^r$ gene in pV1J as the expression construct for gp143. The DNA sequence of pV1Jneo (SEQ.ID.NO.:1) is shown in FIG. 5.

pV1Jneo was further modified to include the human tissue-specific plasminogen activator (tPA) leader. Two synthetic complementary oligomers were annealed and then ligated into pV1Jneo which had been BglII digested. The sense and antisense oligomers were 5'-GATC ACC ATG GAT GCA ATG AAG AGA GGG CTC TGC TGT GTG CTG CTG CTG TGT GGA GCA GTC TTC GTT TCG CCC AGC GA-3', (SEQ.ID.NO.:6) and 5'-GAT CTC GCT GGG CGA AAC GAA GAC TGC TCC ACA CAG CAG CAG CAC ACA GCA GAG CCC TCT CTT CAT TGC ATC CAT GGT-3' (SEQ.ID.NO.:7). These oligomers have overhanging bases compatible for ligation to BglII-cleaved sequences. After ligation the upstream BglII site is destroyed while the downstream BglII is retained for subsequent ligations. Both the junction sites as well as the entire tPA leader sequence were verified by DNA sequencing.

gp143, a carboxyl-terminus truncated form of the Env (gp160) gene from the HIV-1 strain HXB2, was produced from the Env gene found in the plasmid pSP62. pSP62 was constructed in Dr. Robert Gallo's laboratory at the National Institutes of Health, Bethesda, Md., and is available from Biotech Research Laboratories, Inc. pSP62 has a 12.5 kb XbaI fragment of the HXB2 genome subcloned from lambda HXB2. SalI and XbaI digestion of pSP62 yields two HXB2 fragments: 5'-XbaI/SalI, 6.5 kb and 3'-SalI/XbaI, 6 kb. The 3'-SalI/XbaI fragment was subcloned into pUC 18 at the SalI site, yielding pF412. pF412 contains tat/rev/env/nef from HXB2. gp143 was prepared by PCR using plasmid pF412 as template with the following sense and antisense PCR oligomers: 5'-GGT ACA TGA TCA CA GAA AAA TTG TGG GTC ACA GTC-3' (SEQ.ID.NO.:8) and 5'-CCA CAT TGA TCA G CCC GGG C TTA GGG TGA ATA GCC CTG CCT CAC TCT GTT CAC-3' (SEQ.ID.NO.:9). The resulting DNA segment contained BclI restriction sites at either end for cloning into the BclI site of pV1Jneo. Constructs were verified by DNA sequencing of ligation junctions and immunoblot analysis of transfected cells.

HIV structural genes such as Env generally require expression of the HIV regulatory gene rev in order to efficiently produce full-length proteins. This is probably because inhibitory regions (designated INS), which confer rev dependence upon the gp160 transcript, occur at multiple sites within gp160, including the COOH-terminus. gp143 was designed to increase the overall expression levels of Env by eliminating these inhibitory sequences. gp143 also lacks intracellular gp41 regions containing peptide motifs (such as leu-leu) known to cause diversion of membrane proteins to the lysosomes rather than the cell surface. Thus, the use of gp143 in the present invention leads to increased expression of the Env protein both by decreasing rev-dependence and by more efficient transport of protein to the cell surface compared to full-length gp160.

EXAMPLE 4

Production of CHO Cells Expressing gp143

A 2.1 kb NcoIV/SrfI fragment containing a tissue-specific plasminogen activator (tPA) leader sequence and gp143/HXB2 was isolated from pV1Jns-tPA-gp143HXB2 optB (see International Patent Publication WO 94/21797 for a description of the production of pV1Jns-tPA-gp143HXB2 optB) and subcloned into NcoI/EcoRV sites of pLitmus 28 (New England Biolabs). The 2.2 kb XbaI/(SpeI fragment was removed from this vector and subcloned into XbaI sites of pBJ.Neo expression vector (see International Patent Publication WO 97/41154 for a description of the production of pBJ.Neo). The resulting plasmid, pBJ.Neo-tPA-gp143/HXB2 was then transfected into Chinese hamster ovary cells (CHO) using LIPOFECTAMINE PLUS® (Gibco), following the manufacturer's protocol. Briefly, $6 \times 10^5$ CHO cells/well were seeded in 6-well plate (Nunc) twenty four hours prior to transfection. Prior to transfection, cells were washed once with 1 ml of Opti-MEM I (GibcoBRL catalogue number 31985) and left in 0.8 ml per well of the same medium. The plasmid DNA (2 μg) was diluted to 100 μl with Opti-MEM I, mixed with 6 μl of PLUS reagent (GibcoBRL) and incubated at room temperature for 15 minutes. 4 μl of LIPOFECTAMINE® reagent (diluted to 100 μl with Opti-MEM I) was added to the pre-complexed DNA. This final mixture was incubated at room temperature for 15 minutes and added to each well. After 3 hours at 37° C., 5% $CO_2$, 1 ml per well of Opti-MEM I supplemented with 20% Fetal Bovine Serum was added to each well. Forty eight hours later, medium was replaced with Opti-MEM I, 10% Fetal bovine Serum containing 1 mg/ml G418 (GibcoBRL). G418-resistant single cell clones were selected, single cell cloned and expanded.

EXAMPLE 5

Production of Jurkat Cells Expressing β-Lactamase

Jurkat cells expressing β-lactamase can be generated by standard procedures utilizing an expression vector for β-lactamase suitable for mammalian cells. For example, the following method can be used. 20 μg of DNA, pcDNA3-BlaM (Aurora Biosciences, San Diego, Calif.) was added to 0.8 mls of Jurkat cells ($6.25 \times 10^6$/ml) in medium (RPMI 1640 lacking HEPES: GIBCO number 11875) in a GENE PULSER® cuvette (Bio-Rad catalogue number 165-2088) and allowed to incubate on ice for 10 minutes. Cells were electroporated at 290 volt, 960 μF for approximately 18 seconds. Following a 10 minute incubation on ice, cells were transferred to a T75 flask containing RPMI 1640 with 25 mM HEPES, 10% heat inactivated fetal bovine serum, 2 mM L-glutamine, 0.1 mM non-essential amino acids, 1 mM sodium pyruvate, and 55 □M 2-mercaptoethanol and cultured at 37° C. Thirty six hours later cells were transferred to fresh medium supplemented with 0.7 mg/l ml G418. Individual clones were selected by single cell cloning. Clones expressing β-lactamase were selected as those that fluoresce blue when visualized under the fluorescent microscope after loading with CCF2/AM. as described above.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed:

1. A method for determining fusion between two cell types via the measurement of fluorescence resonance energy transfer (FRET) comprising:
   (a) providing a first cell that expresses β-lactamase;
   (b) providing a second cell that does not express β-lactamase but contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where FRET can occur when the linker is intact but does not occur when the linker has been cleaved;
   (c) measuring the amount of FRET from the substrate in the second cell in the absence of fusion between the first and second cells;
   (d) bringing the first and second cells into contact under conditions such that fusion occurs; and
   (e) measuring the amount of FRET from the substrate after fusion has occurred;
   where the ratio of the amount of FRET measured in step (e) to the amount of FRET measured in step (c) represents the amount of fusion that has occurred, with smaller ratios indicating greater amounts of fusion.

2. A method of claim 1 where said fusion is determined by measuring the donor/acceptor emission ratio from the fluorescent substrate in the absence of and after fusion between the first and second cells, and where the ratio of said donor/acceptor emission ratio measured after fusion over the donor/acceptor emission ratio in the absence of fusion represents the amount of fusion that has occurred, with larger ratios indicating greater amounts of fusion between the two cell types.

3. A method for identifying inhibitors of the fusion of a first and a second cell type comprising:
   (a) providing a first cell that expresses β-lactamase;
   (b) providing a second cell that does not express β-lactamase but contains a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved;
   (c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance; and
   (d) measuring the amount of FRET in step (c) in the presence and in the absence of the substance;
   where if the amount of FRET is greater in the presence of the substance than in the absence of the substance, then the substance is an inhibitor of the fusion of the first and the second cells.

4. A method of claim 3 wherein said first cell that expresses β-lactamase also expresses CD4 and a chemokine receptor.

5. A method of claim 3 wherein said first cell that expresses β-lactamase also expresses a viral protein that mediates fusion and said second cell that does not express β-lactamase also expresses CD4 and a chemokine receptor.

6. A method of identifying an inhibitor of the fusion of a first and a second cell type comprising:
   (a) providing a first cell that expresses β-lactamase where the first cell is a suspension cell;
   (b) providing a second cell that does not express β-lactamase where the second cell is an adherent cell;
   (c) bringing a portion of the first and second cells into contact in the presence and a portion of the first and second cells into contact in the absence of a substance suspected of being an inhibitor of the fusion of the first and the second cells under conditions and for such a time that fusion between the first and second cells will occur in the absence of the substance;

(d) washing away any unfused first cells;

(e) exposing the cells after step (d) to a fluorescent substrate of β-lactamase where the substrate is a compound comprising two fluorescent moieties that are connected by a linker that is susceptible to cleavage by β-lactamase where the emission spectrum of one moiety overlaps the absorption spectrum of the other moiety and where fluorescence resonance energy transfer (FRET) can occur when the linker is intact but does not occur when the linker has been cleaved under conditions and for a sufficient time such that the substrate is taken up into the cytoplasm of the fused cells and into the cytoplasm of any unfused adherent cells;

(f) washing away any substrate that has not been taken up by the fused cells or any unfused adherent cells; and (g) measuring the amount of FRET from the substrate in the fused cells and in any unfused adherent cells;

where if the amount of FRET is greater in the presence of the substance than in the absence of the substance, then the substance is an inhibitor of the fusion of the first and the second cells.

7. The method of claim 6 where:

(i) the first cell is a Jurkat T cell;

(ii) the second cell is a CHO cell or a 293T cell;

(iii) the first cell expresses human CD4 and a human chemokine receptor that is selected from the group consisting of: CCR5, CXCR4, CX3CR1, CCR8, CCR2B, CCR9, CCR3, STRL33/BONZO, GPR15/BOB, and APJ;

(iv) the second cell expresses an HIV-1 Env protein; and (v) the substrate of β-lactamase is CCF2/AM.

8. The method of claim 7 where said HIV-1 Env protein is gp143.

9. A method of claim 6 where said first cell that expresses β-lactamase also expresses CD4 and a chemokine receptor and where said second cell that does not express β-lactamase expresses a viral protein that mediates fusion of the first and the second cells.

10. A method of claim 6 where said inhibitors are identified by measuring the donor/acceptor emission ratio from the fluorescent substrate in the presence of and absence of the substance, and where if said donor/acceptor emission ratio is smaller in the presence of the substance, then the substance is an inhibitor of the fusion of the first and second cells.

* * * * *

SEQUENCE LISTING

<160> NUMBER OF SEQ ID NOS: 9

<210> SEQ ID NO 1
<211> LENGTH: 4865
<212> TYPE: DNA
<213> ORGANISM: Artificial Sequence
<220> FEATURE:

<223> OTHER INFORMATION: Cloning Vector

<400> SEQUENCE: 1

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgct | gcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcagattgg | 240 |
| ctattggcca | ttgcatacgt | tgtatccata | tcataatatg | tacatttata | ttggctcatg | 300 |
| tccaacatta | ccgccatgtt | gacattgatt | attgactagt | tattaatagt | aatcaattac | 360 |
| ggggtcatta | gttcatagcc | catatatgga | gttccgcgtt | acataactaa | cggtaaatgg | 420 |
| cccgcctggc | tgaccgccca | acgacccccg | cccattgacg | tcaataatga | cgtatgttcc | 480 |
| catagtaacg | ccaataggga | ctttccattg | acgtcaatgg | gtggagtatt | tacggtaaac | 540 |
| tgcccacttg | gcagtacatc | aagtgtatca | tatgccaagt | acgccccta | ttgacgtcaa | 600 |
| tgacggtaaa | tggcccgcct | ggcattatgc | ccagtacatg | accttatggg | actttcctac | 660 |
| ttggcagtac | atctacgtat | tagtcatcgc | tattaccatg | gtgatgcggt | tttggcagta | 720 |
| catcaatggg | cgtggatagc | ggtttgactc | acggggattt | ccaagtctcc | accccattga | 780 |
| cgtcaatggg | agtttgtttt | ggcaccaaaa | tcaacgggac | tttccaaaat | gtcgtaacaa | 840 |
| ctccgcccca | ttgacgcaaa | tgggcggtag | gcgtgtacgg | tgggaggtct | atataagcag | 900 |
| agctcgttta | gtgaaccgtc | agatcgcctg | gagacgccat | ccacgctgtt | ttgacctcca | 960 |
| tagaagacac | cgggaccgat | ccagcctccg | cggccgggaa | cggtgcattg | gaacgcggat | 1020 |
| tccccgtgcc | aagagtgacg | taagtacccg | cctatagagt | ctataggccc | acccctggc | 1080 |
| ttcttatgca | tgctatactg | tttttggctt | ggggtctata | caccccgct | tcctcatgtt | 1140 |
| ataggtgatg | gtatagctta | gcctataggt | gtgggttatt | gaccattatt | gaccactccc | 1200 |
| ctattggtga | cgatactttc | cattactaat | ccataacatg | gctctttgcc | acaactctct | 1260 |
| ttattggcta | tatgccaata | cactgtcctt | cagagactga | cacggactct | gtatttttac | 1320 |
| aggatggggt | ctcatttatt | atttacaaat | tcacatatac | aacaccaccg | tccccagtgc | 1380 |
| ccgcagtttt | tattaaacat | aacgtgggat | ctccacgcga | atctcgggta | cgtgttccgg | 1440 |
| acatgggctc | ttctccggta | gcggcggagc | ttctacatcc | gagccctgct | cccatgcctc | 1500 |
| cagcgactca | tggtcgctcg | gcagctcctt | gctcctaaca | gtggaggcca | gacttaggca | 1560 |
| cagcacgatg | cccaccacca | ccagtgtgcc | gcacaaggcc | gtggcggtag | ggtatgtgtc | 1620 |
| tgaaaatgag | ctcggggagc | gggcttgcac | cgctgacgca | tttggaagac | ttaaggcagc | 1680 |
| ggcagaagaa | gatgcaggca | gctgagttgt | tgtgttctga | taagagtcag | aggtaactcc | 1740 |
| cgttgcggtg | ctgttaacgg | tggagggcag | tgtagtctga | gcagtactcg | ttgctgccgc | 1800 |
| gcgcgccacc | agacataata | gctgacagac | taacagactt | tcctttcca | tgggtctttt | 1860 |
| ctgcagtcac | cgtccttgag | atctgctgtg | ccttctagtt | gccagccatc | tgttgtttgc | 1920 |
| ccctcccccg | tgccttcctt | gaccctggaa | ggtgccactc | ccactgtcct | ttcctaataa | 1980 |
| aatgaggaaa | ttgcatcgca | ttgtctgagt | aggtgtcatt | ctattctggg | ggtgggtg | 2040 |
| gggcagcaca | gcaaggggga | ggattgggaa | gacaatagca | ggcatgctgg | ggatgcggtg | 2100 |
| ggctctatgg | gtacccaggt | gctgaagaat | tgacccggtt | cctcctgggc | cagaaagaag | 2160 |
| caggcacatc | cccttctctg | tgacacaccc | tgtccacgcc | cctggttctt | agttccagcc | 2220 |
| ccactcatag | gacactcata | gctcaggagg | gctccgcctt | caatcccacc | cgctaaagta | 2280 |

```
cttggagcgg tctctccctc cctcatcagc ccaccaaacc aaacctagcc tccaagagtg    2340
ggaagaaatt aaagcaagat aggctattaa gtgcagaggg agagaaaatg cctccaacat    2400
gtgaggaagt aatgagagaa atcatagaat ttcttccgct tcctcgctca ctgactcgct    2460
gcgctcggtc gttcggctgc ggcgagcggt atcagctcac tcaaaggcgg taatacggtt    2520
atccacagaa tcaggggata acgcaggaaa gaacatgtga gcaaaaggcc agcaaaaggc    2580
caggaaccgt aaaaaggccg cgttgctggc gtttttccat aggctccgcc cccctgacga    2640
gcatcacaaa aatcgacgct caagtcagag gtggcgaaac ccgacaggac tataaagata    2700
ccaggcgttt ccccctggaa gctccctcgt gcgctctcct gttccgaccc tgccgcttac    2760
cggatacctg tccgcctttc tcccttcggg aagcgtggcg ctttctcaat gctcacgctg    2820
taggtatctc agttcggtgt aggtcgttcg ctccaagctg ggctgtgtgc acgaaccccc    2880
cgttcagccc gaccgctgcg ccttatccgg taactatcgt cttgagtcca acccggtaag    2940
acacgactta tcgccactgg cagcagccac tggtaacagg attagcagag cgaggtatgt    3000
aggcggtgct acagagttct tgaagtggtg gcctaactac ggctacacta aggacagt    3060 atttggtatc tgcgctctgc tgaagccagt taccttcgga aaaagagttg gtagctcttg    3120
atccggcaaa caaaccaccg ctggtagcgg tggtttttt gtttgcaagc agcagattac    3180
gcgcagaaaa aaaggatctc aagaagatcc tttgatcttt tctacggggt ctgacgctca    3240
gtggaacgaa aactcacgtt aagggatttt ggtcatgaga ttatcaaaaa ggatcttcac    3300
ctagatcctt ttaaattaaa aatgaagttt taaatcaatc taaagtatat atgagtaaac    3360
ttggtctgac agttaccaat gcttaatcag tgaggcacct atctcagcga tctgtctatt    3420
tcgttcatcc atagttgcct gactccgggg ggggggggcg ctgaggtctg cctcgtgaag    3480
aaggtgttgc tgactcatac caggcctgaa tcgccccatc atccagccag aaagtgaggg    3540
agccacggtt gatgagagct tgttgtagg tggaccagtt ggtgattttg aacttttgct    3600
ttgccacgga acgtctgcg ttgtcgggaa gatgcgtgat ctgatccttc aactcagcaa    3660
aagttcgatt tattcaacaa agccgccgtc cgtcaagtc agcgtaatgc tctgccagtg    3720
ttacaaccaa ttaaccaatt ctgattagaa aaactcatcg agcatcaaat gaaactgcaa    3780
tttattcata tcaggattat caataccata ttttgaaaa agccgtttct gtaatgaagg    3840
agaaaactca ccgaggcagt tccataggat ggcaagatcc tggtatcggt ctgcgattcc    3900
gactcgtcca acatcaatac aacctattaa tttcccctcg tcaaaaataa ggttatcaag    3960
tgagaaatca ccatgagtga cgactgaatc cggtgagaat ggcaaaagct tatgcatttc    4020
tttccagact tgttcaacag gccagccatt acgctcgtca tcaaaatcac tcgcatcaac    4080
caaaccgtta ttcattcgtg attgcgcctg agcgagacga atacgcgat cgctgttaaa    4140 aggacaatta caaacaggaa tcgaatgcaa ccggcgcagg aacactgcca gcgcatcaac    4200
aatattttca cctgaatcag gatattcttc taatacctgg aatgctgttt tcccggggat    4260
cgcagtggtg agtaaccatg catcatcagg agtacggata aaatgcttga tggtcggaag    4320
aggcataaat tccgtcagcc agtttagtct gaccatctca tctgtaacat cattggcaac    4380
gctacctttg ccatgtttca gaaacaactc tggcgcatcg gcttcccat acaatcgata    4440 gattgtcgca cctgattgcc cgacattatc gcgagcccat ttatacccat ataaatcagc    4500
atccatgttg gaatttaatc gcggcctcga gcaagacgtt tcccgttgaa tatggctcat    4560
aacaccccct gtattactgt ttatgtaagc agacagtttt attgttcatg atgatatatt    4620
```

```
tttatcttgt gcaatgtaac atcagagatt ttgagacaca acgtggcttt ccccccccc       4680 ccattattga agcatttatc agggttattg tctcatgagc ggatacatat ttgaatgtat      4740
ttagaaaaat aaacaaatag gggttccgcg cacatttccc cgaaaagtgc cacctgacgt      4800
ctaagaaacc attattatca tgacattaac ctataaaaat aggcgtatca ccaggccctt      4860
tcgtc                                                                 4865

<210> SEQ ID NO 2
<211> LENGTH: 29
<212> TYPE: DNA
<213> ORGANISM: Artificial Sequence
<220> FEATURE:
<223> OTHER INFORMATION: PCR Probe

<400> SEQUENCE: 2
gagactcgag agagcaccat ggacccagg                                         29

<210> SEQ ID NO 3
<211> LENGTH: 30
<212> TYPE: DNA
<213> ORGANISM: Artificial Sequence
<220> FEATURE:
<223> OTHER INFORMATION: PCR Probe

<400> SEQUENCE: 3
gagagaattc ctacggggag aaggttgtgg                                        30

<210> SEQ ID NO 4
<211> LENGTH: 26
<212> TYPE: DNA
<213> ORGANISM: Artificial Sequence
<220> FEATURE:
<223> OTHER INFORMATION: PCR Probe

<400> SEQUENCE: 4
gaaagagcag aagacagtgg caatga                                            26

<210> SEQ ID NO 5
<211> LENGTH: 40
<212> TYPE: DNA
<213> ORGANISM: Artificial Sequence
<220> FEATURE:
<223> OTHER INFORMATION: PCR Probe

<400> SEQUENCE: 5
gggctttgct aaatgggtgg caagtggccc gggcatgtgg                             40

<210> SEQ ID NO 6
<211> LENGTH: 78
<212> TYPE: DNA
<213> ORGANISM: Human

<400> SEQUENCE: 6
gatcaccatg gatgcaatga agagagggct ctgctgtgtg ctgctgctgt gtggagcagt      60
cttcgtttcg cccagcga                                                    78

<210> SEQ ID NO 7
<211> LENGTH: 78
<212> TYPE: DNA
<213> ORGANISM: Human

<400> SEQUENCE: 7
gatctcgctg ggcgaaacga agactgctcc acacagcagc agcacacagc agagccctct      60
```

-continued

```
cttcattgca tccatggt                                                    78

<210> SEQ ID NO 8
<211> LENGTH: 35
<212> TYPE: DNA
<213> ORGANISM: Artificial Sequence
<220> FEATURE:
<223> OTHER INFORMATION: PCR Primer

<400> SEQUENCE: 8
ggtacatgat cacagaaaaa ttgtgggtca cagtc                                 35

<210> SEQ ID NO 9
<211> LENGTH: 53
<212> TYPE: DNA
<213> ORGANISM: Artificial Sequence
<220> FEATURE:
<223> OTHER INFORMATION: PCR Primer

<400> SEQUENCE: 9
ccacattgat cagcccgggc ttagggtgaa tagccctgcc tcactctgtt cac             53
```